(12) United States Patent
Alden et al.

(10) Patent No.: US 7,909,775 B2
(45) Date of Patent: Mar. 22, 2011

(54) METHOD AND APPARATUS FOR LANCET LAUNCHING DEVICE INTEGRATED ONTO A BLOOD-SAMPLING CARTRIDGE

(75) Inventors: Don Alden, Sunnyvale, CA (US); Dominique M. Freeman, La Honda, CA (US); Paul Lum, Los Altos, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 845 days.

(21) Appl. No.: 11/768,641

(22) Filed: Jun. 26, 2007

(65) Prior Publication Data

US 2007/0249963 A1 Oct. 25, 2007

Related U.S. Application Data

(62) Division of application No. 10/363,510, filed as application No. PCT/US02/19060 on Jun. 12, 2002, now Pat. No. 7,749,174.

(60) Provisional application No. 60/297,860, filed on Jun. 12, 2001.

(51) Int. Cl.
*A61B 5/00* (2006.01)
(52) U.S. Cl. .................. 600/573; 606/181
(58) Field of Classification Search ............ 606/181, 606/182; 600/573, 575, 578, 583, 584
See application file for complete search history.

(56) References Cited

U.S. PATENT DOCUMENTS

| 2,061 | A | 4/1841 | Osdel ........................... 606/182 |
|---|---|---|---|
| 55,620 | A | 6/1866 | Capewell ...................... 606/181 |
| 657,646 | A | 9/1900 | Haviland ........................ 435/4 |
| 1,135,465 | A | 4/1915 | Pollock ......................... 606/181 |
| 1,733,847 | A | 10/1929 | Wilmot |
| 2,258,857 | A | 10/1941 | McCann ......................... 601/81 |
| 2,628,319 | A | 2/1953 | Vang .............................. 310/15 |
| 2,714,890 | A | 8/1955 | Alfred ........................... 606/169 |
| 2,763,935 | A | 9/1956 | Whaley ........................... 33/511 |
| 2,801,633 | A | 8/1957 | Mauze et al. |
| 3,046,987 | A | 7/1962 | Ehrlich ......................... 128/314 |
| 3,030,959 | A | 9/1962 | Grunert ......................... 128/329 |
| 3,086,288 | A | 4/1963 | Balamuth ..................... 30/277.4 |
| 3,208,452 | A | 9/1965 | Stern ............................ 606/182 |
| 3,358,689 | A | 12/1967 | Higgins ........................ 128/329 |
| 3,412,729 | A | 11/1968 | Smith, Jr. ..................... 128/2.05 |
| 3,448,307 | A | 6/1969 | Rudolph ......................... 310/23 |
| 3,494,358 | A | 2/1970 | Grossenbacher ............. 128/218 |
| 3,620,209 | A | 11/1971 | Kravitz .......................... 601/79 |
| 3,626,929 | A | 12/1971 | Sanz ............................ 128/2 R |
| 3,628,026 | A | 12/1971 | Cronin ....................... 250/214.1 |
| 3,665,672 | A | 5/1972 | Speelman ........................ 53/435 |
| 3,673,475 | A | 6/1972 | Britton ......................... 318/122 |

(Continued)

FOREIGN PATENT DOCUMENTS

DE 2206674 8/1972

(Continued)

*Primary Examiner* — Michael J Milano
*Assistant Examiner* — Victor X Nguyen
(74) *Attorney, Agent, or Firm* — Paul Davis; Goodwin Procter LLP

(57) ABSTRACT

A method and apparatus (2) for obtaining a sample of blood. An embodiment includes of an apparatus (2) which integrates lancing (12), sample collection, and analysis. The presence of patients finger on the active sampling area can be sensed by monitoring the pressure applied by the finger on the device (2).

4 Claims, 4 Drawing Sheets

U.S. PATENT DOCUMENTS

| | | | |
|---|---|---|---|
| 3,712,292 A | 1/1973 | Mielke, Jr. | 128/2 G |
| 3,712,293 A | 1/1973 | Mielke, Jr. | 128/2 |
| 3,734,812 A | 5/1973 | Yazawa | 428/107 |
| 3,742,954 A | 7/1973 | Strickland | 128/302 |
| 3,780,960 A | 12/1973 | Tokuno | 242/555.2 |
| 3,832,776 A | 9/1974 | Sawyer | 30/272 |
| 3,836,148 A | 9/1974 | Manning | 273/368 |
| 3,851,543 A | 12/1974 | Krom | 74/493 |
| 3,853,010 A | 12/1974 | Christen | 73/864.24 |
| 3,924,818 A | 12/1975 | Pfeifle | 242/364.7 |
| 3,938,526 A | 2/1976 | Anderson | 128/303.1 |
| 3,953,172 A | 4/1976 | Shapiro | 23/230 |
| 3,971,365 A | 7/1976 | Smith | 128/2.17 |
| 4,057,394 A | 11/1977 | Genshaw | 23/230 |
| 4,077,406 A | 3/1978 | Sandhage | 604/61 |
| 4,109,655 A | 8/1978 | Chaconac | 128/253 |
| 4,139,011 A | 2/1979 | Benoit | 606/182 |
| 4,154,228 A | 5/1979 | Feldstein | 606/169 |
| 4,168,130 A | 9/1979 | Barth | 404/99 |
| 4,184,486 A | 1/1980 | Papa | 600/373 |
| 4,190,420 A | 2/1980 | Covington | 422/63 |
| 4,191,193 A | 3/1980 | Seo | 600/488 |
| 4,193,690 A | 3/1980 | Levenson | 356/301 |
| 4,203,446 A | 5/1980 | Hofert | 606/182 |
| 4,207,870 A | 6/1980 | Eldridge | 128/766 |
| 4,223,674 A | 9/1980 | Fluent | 604/504 |
| 4,224,125 A | 9/1980 | Nakamura | 204/195 B |
| 4,224,949 A | 9/1980 | Scott | 128/734 |
| 4,230,118 A | 10/1980 | Holman et al. | 128/314 |
| 4,240,439 A | 12/1980 | Abe | 600/412 |
| 4,254,083 A | 3/1981 | Columbus | 422/55 |
| 4,258,001 A | 3/1981 | Pierce | 422/56 |
| 4,259,653 A | 3/1981 | McGonigal | 310/15 |
| 4,299,230 A | 11/1981 | Kubota | 600/300 |
| 4,301,412 A | 11/1981 | Hill | 324/442 |
| 4,321,397 A | 3/1982 | Nix | 548/366 |
| 4,338,174 A | 7/1982 | Tamura | 204/195 |
| 4,340,669 A | 7/1982 | Bauer | 435/14 |
| 4,350,762 A | 9/1982 | De Luca | 435/10 |
| 4,353,984 A | 10/1982 | Yamada | 435/14 |
| 4,356,826 A | 11/1982 | Kubota | 600/300 |
| 4,360,016 A | 11/1982 | Sarrine | 128/763 |
| 4,388,922 A | 6/1983 | Telang | 604/319 |
| 4,391,905 A | 7/1983 | Bauer | 435/14 |
| 4,391,906 A | 7/1983 | Bauer | 435/14 |
| 4,392,933 A | 7/1983 | Nakamura | 204/403.14 |
| 4,394,512 A | 7/1983 | Batz | 548/365 |
| 4,397,556 A | 8/1983 | Muller | 356/301 |
| 4,407,008 A | 9/1983 | Schmidt | 356/301 |
| 4,411,266 A | 10/1983 | Cosman | 128/303.18 |
| 4,414,975 A | 11/1983 | Ryder | 128/314 |
| 4,418,037 A | 11/1983 | Katsuyama | 422/56 |
| 4,420,564 A | 12/1983 | Tsuji | 435/288 |
| 4,425,039 A | 1/1984 | Grant | 356/35.5 |
| 4,426,451 A | 1/1984 | Columbus | 436/518 |
| 4,426,884 A | 1/1984 | Polchaninoff | 73/172 |
| 4,440,301 A | 4/1984 | Intengan | 206/456 |
| 4,442,836 A | 4/1984 | Meinecke | 128/314 |
| 4,442,972 A | 4/1984 | Sahay | 236/1 EA |
| 4,449,529 A | 5/1984 | Burns | 606/182 |
| 4,462,405 A | 7/1984 | Ehrlich | 606/182 |
| 4,469,110 A | 9/1984 | Slama | 128/770 |
| 4,517,978 A | 5/1985 | Levin | 128/314 |
| 4,518,384 A | 5/1985 | Tarello. | 604/61 |
| 4,523,994 A | 6/1985 | Shono | 549/352 |
| 4,535,769 A | 8/1985 | Burns | 128/314 |
| 4,535,773 A | 8/1985 | Yoon | 606/185 |
| 4,537,197 A | 8/1985 | Hulka | 128/633 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,561,445 A | 12/1985 | Berke | 128/642 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,586,819 A | 5/1986 | Tochigi | 356/301 |
| 4,590,411 A | 5/1986 | Kelly | 318/687 |
| 4,595,479 A | 6/1986 | Kimura | 204/294 |
| 4,600,014 A | 7/1986 | Beraha | 128/754 |
| 4,603,209 A | 7/1986 | Tsien | 549/352 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia | 600/583 |
| 4,637,393 A | 1/1987 | Ray | 128/305 |
| 4,637,403 A | 1/1987 | Garcia | 600/583 |
| 4,643,189 A | 2/1987 | Mintz | 128/314 |
| 4,648,408 A | 3/1987 | Hutcheson | 128/770 |
| 4,648,714 A | 3/1987 | Benner | 356/301 |
| 4,653,511 A | 3/1987 | Goch | 128/763 |
| 4,653,513 A | 3/1987 | Dombrowski | 600/578 |
| 4,655,225 A | 4/1987 | Dahne | 600/316 |
| 4,661,768 A | 4/1987 | Carusillo | |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |
| 4,714,462 A | 12/1987 | DiDomenico | 604/67 |
| 4,715,374 A | 12/1987 | Maggio | 128/314 |
| 4,731,330 A | 3/1988 | Hill | 436/16 |
| 4,731,726 A | 3/1988 | Allen | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults et al. | 435/291 |
| 4,758,323 A | 7/1988 | Davis | 204/403 |
| 4,774,192 A | 9/1988 | Teriniello | 436/530 |
| 4,784,486 A | 11/1988 | Van Wagenen | 356/301 |
| 4,787,398 A | 11/1988 | Garcia | 600/583 |
| 4,790,979 A | 12/1988 | Teriniello | 422/56 |
| 4,794,926 A | 1/1989 | Munsch et al. | 606/183 |
| 4,797,283 A | 1/1989 | Allen | 424/443 |
| RE32,922 E | 3/1989 | Levin | 128/314 |
| 4,814,142 A | 3/1989 | Gleisner | 422/56 |
| 4,814,661 A | 3/1989 | Ratzlaff | 310/328 |
| 4,817,603 A | 4/1989 | Turner | 606/182 |
| 4,818,493 A | 4/1989 | Coville | 422/102 |
| 4,820,010 A | 4/1989 | Sciefres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeil | 435/53 |
| 4,836,904 A | 6/1989 | Armstron | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 469,265 A | 9/1989 | McEwen | 128/774 |
| 4,868,129 A | 9/1989 | Gibbons | 436/512 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |

| Patent | Kind | Date | Inventor | Class |
|---|---|---|---|---|
| 4,900,424 | A | 2/1990 | Birch | 204/409 |
| 4,900,666 | A | 2/1990 | Phillips | 435/25 |
| 4,911,794 | A | 3/1990 | Parce | 204/1 T |
| 4,920,977 | A | 5/1990 | Haynes | 128/770 |
| 4,924,879 | A | 5/1990 | O'Brien | |
| 4,935,346 | A | 6/1990 | Phillips | 435/14 |
| 4,938,218 | A | 7/1990 | Goodman | 128/633 |
| 4,940,468 | A | 7/1990 | Petilo | 606/170 |
| 4,944,304 | A | 7/1990 | Nishina | 128/667 |
| 4,945,045 | A | 7/1990 | Forrest | 435/25 |
| 4,946,795 | A | 8/1990 | Gibbons | 436/179 |
| 4,948,727 | A | 8/1990 | Cass | 435/18 |
| 4,948,961 | A | 8/1990 | Hillman | 250/252.1 |
| 4,952,373 | A | 8/1990 | Sugarman | 422/99 |
| 4,952,515 | A | 8/1990 | Gleisner | 436/169 |
| 4,953,552 | A | 9/1990 | DeMarzo | 128/635 |
| 4,953,976 | A | 9/1990 | Adler-Golden | 356/301 |
| 4,963,498 | A | 10/1990 | Hillman | 436/69 |
| 4,966,581 | A | 10/1990 | Landau | 604/72 |
| 4,966,646 | A | 10/1990 | Zdeblick | 156/633 |
| 4,966,671 | A | 10/1990 | Nylander | 204/153.14 |
| 4,975,581 | A | 12/1990 | Robinson | 250/339 |
| 4,976,724 | A | 12/1990 | Nieto | 606/182 |
| 4,977,910 | A | 12/1990 | Miyahara | 134/7 |
| 4,983,178 | A | 1/1991 | Schnell | 606/181 |
| 4,984,085 | A | 1/1991 | Landowski | 358/213 |
| 4,990,154 | A | 2/1991 | Brown | 606/182 |
| 4,995,402 | A | 2/1991 | Smith | 600/584 |
| 4,999,582 | A | 3/1991 | Parks | 324/438 |
| 5,001,054 | A | 3/1991 | Wagner | 435/14 |
| 5,001,873 | A | 3/1991 | Rufin | 451/39 |
| 5,004,923 | A | 4/1991 | Hillman | 250/341 |
| 5,010,772 | A | 4/1991 | Bourland | 73/862.04 |
| 5,010,774 | A | 4/1991 | Kikuo | 73/862.04 |
| 5,014,718 | A | 5/1991 | Mitchen | 128/771 |
| 5,019,974 | A | 5/1991 | Beckers | 364/413.02 |
| 5,026,388 | A | 6/1991 | Ingalz | 606/182 |
| D318,331 | S | 7/1991 | Phillips | D24/169 |
| 5,028,142 | A | 7/1991 | Vladimir | 250/341 |
| 5,029,583 | A | 7/1991 | Meserol | |
| 5,035,704 | A | 7/1991 | Lambert | 606/182 |
| 5,039,617 | A | 8/1991 | McDonald | 436/69 |
| 5,043,143 | A | 8/1991 | Shaw | 422/65 |
| 5,046,496 | A | 9/1991 | Betts | 600/352 |
| 5,047,044 | A | 9/1991 | Smith et al. | |
| 5,049,373 | A | 9/1991 | Tsien | 549/352 |
| 5,049,487 | A | 9/1991 | Phillips | 435/4 |
| 5,054,487 | A | 10/1991 | Clarke | 128/633 |
| 5,054,499 | A | 10/1991 | Swierczek | 128/770 |
| 5,057,082 | A | 10/1991 | Burchette, Jr. | 604/164 |
| 5,057,277 | A | 10/1991 | Mauze | 422/56 |
| 5,059,394 | A | 10/1991 | Phillips | 422/68.1 |
| 5,059,789 | A | 10/1991 | Salcudean | 250/206.1 |
| 5,060,174 | A | 10/1991 | Gross | 702/139 |
| 5,062,898 | A | 11/1991 | McDermott | 134/7 |
| 5,070,874 | A | 12/1991 | Barnes | 128/633 |
| 5,070,886 | A | 12/1991 | Mitchen | 128/771 |
| 5,074,872 | A | 12/1991 | Brown | 606/182 |
| 5,077,017 | A | 12/1991 | Gorin | 422/100 |
| 5,077,199 | A | 12/1991 | Basagni | 435/14 |
| 5,080,865 | A | 1/1992 | Leiner | 422/68.1 |
| 5,086,229 | A | 2/1992 | Rosenthal | 250/341 |
| 5,089,112 | A | 2/1992 | Skotheim | 204/403 |
| 5,092,842 | A | 3/1992 | Bechtold | 604/135 |
| 5,094,943 | A | 3/1992 | Siedel | 435/25 |
| 5,096,669 | A | 3/1992 | Lauks | 204/403.02 |
| 5,097,810 | A | 3/1992 | Fishman | 600/556 |
| 5,100,427 | A | 3/1992 | Crossman | 606/182 |
| 5,100,428 | A | 3/1992 | Mumford | 606/182 |
| 5,104,380 | A | 4/1992 | Holman | 604/117 |
| 5,104,619 | A | 4/1992 | Castro | 422/56 |
| 5,104,813 | A | 4/1992 | Besemer | 436/179 |
| 5,107,764 | A | 4/1992 | Gasparrini | 101/425 |
| 5,108,564 | A | 4/1992 | Szuminsky | 204/153.12 |
| 5,108,889 | A | 4/1992 | Smith et al. | |
| 5,116,759 | A | 5/1992 | Klainer | 435/288 |
| 5,120,420 | A | 6/1992 | Nankai | 204/403 |
| 5,122,244 | A | 6/1992 | Hoenes | 204/153 |
| 5,126,034 | A | 6/1992 | Carter | 204/403 |
| 5,128,015 | A | 7/1992 | Szuminsky | 204/403 |
| 5,128,171 | A | 7/1992 | Gleisner | 427/2 |
| 5,132,801 | A | 7/1992 | Yamano | 358/213 |
| 5,133,730 | A | 7/1992 | Biro | 606/182 |
| 5,135,719 | A | 8/1992 | Hillman | 422/101 |
| 5,139,685 | A | 8/1992 | Castro | 210/767 |
| 5,140,161 | A | 8/1992 | Hillman | 250/341 |
| 5,141,868 | A | 8/1992 | Shanks | 435/288 |
| 5,144,139 | A | 9/1992 | Hillman | 250/341 |
| 5,145,565 | A | 9/1992 | Kater | 600/341 |
| 5,146,091 | A | 9/1992 | Knudson | 250/341.6 |
| 5,152,296 | A | 10/1992 | Simons | 128/670 |
| 5,152,775 | A | 10/1992 | Ruppert | 606/182 |
| 5,153,671 | A | 10/1992 | Miles | 356/301 |
| 5,156,611 | A | 10/1992 | Haynes | 606/181 |
| 5,162,525 | A | 11/1992 | Masilamani | 549/352 |
| 5,163,442 | A | 11/1992 | Ono | 128/760 |
| 5,164,598 | A | 11/1992 | Hillman | 250/341 |
| 5,167,619 | A | 12/1992 | Wuchinich | 604/22 |
| 5,170,364 | A | 12/1992 | Gross | 702/139 |
| 5,174,726 | A | 12/1992 | Findlay | 417/205 |
| D332,490 | S | 1/1993 | Brown | D24/146 |
| 5,178,142 | A | 1/1993 | Harjunmaa | 128/633 |
| 5,179,005 | A | 1/1993 | Phillips | 435/14 |
| 5,181,910 | A | 1/1993 | Scanlon | 604/67 |
| 5,181,914 | A | 1/1993 | Zook | 604/307 |
| 5,183,042 | A | 2/1993 | Harjunmaa | 128/633 |
| 5,185,256 | A | 2/1993 | Nankai | 435/174 |
| 5,187,100 | A | 2/1993 | Matzinger | 436/16 |
| 5,188,118 | A | 2/1993 | Terwilliger | 600/566 |
| 5,189,751 | A | 3/1993 | Giuliani | 15/22.1 |
| 5,192,415 | A | 3/1993 | Yoshioka | 204/403 |
| 5,194,391 | A | 3/1993 | Mauze | 436/166 |
| 5,196,025 | A | 3/1993 | Ranalletta | 606/182 |
| 5,201,324 | A | 4/1993 | Swierczek | 128/770 |
| 5,205,920 | A | 4/1993 | Oyama | 204/403 |
| 5,209,028 | A | 5/1993 | McDermott | 51/426 |
| 5,211,652 | A | 5/1993 | Derbyshire | 606/182 |
| 5,212,879 | A | 5/1993 | Biro | 29/437 |
| 5,215,587 | A | 6/1993 | McConnellogue | 118/699 |
| 5,216,597 | A | 6/1993 | Beckers | 364/413.02 |
| 5,217,480 | A | 6/1993 | Haber | 606/182 |
| 5,218,966 | A | 6/1993 | Yamasawa | 600/499 |
| 5,222,504 | A | 6/1993 | Solomon | 600/557 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber et al. | 128/770 |
| 5,241,969 | A | 9/1993 | Carson | 600/566 |
| 5,247,932 | A | 9/1993 | Chung | 128/633 |
| 5,249,583 | A | 10/1993 | Mallaby | 600/567 |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| 5,266,359 | A | 11/1993 | Spielvogel | 427/388.4 |
| D342,673 | S | 12/1993 | Cerola | D24/147 |
| 5,272,087 | A | 12/1993 | El Murr | 435/291 |
| 5,277,181 | A | 1/1994 | Mendelson | 128/633 |
| 5,279,294 | A | 1/1994 | Anderson | 600/322 |
| 5,279,791 | A | 1/1994 | Aldrich | 422/58 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollmann | 435/288 |
| 5,294,261 | A | 3/1994 | McDermott | 134/7 |
| 5,296,378 | A | 3/1994 | Sakata | 436/63 |
| 5,300,779 | A | 4/1994 | Hillman | 250/341 |
| 5,304,192 | A | 4/1994 | Crouse | 606/181 |
| 5,304,193 | A | 4/1994 | Zhadanov | 606/182 |
| 5,304,347 | A | 4/1994 | Mann | 422/67 |
| 5,304,468 | A | 4/1994 | Phillips | 435/14 |
| 5,306,623 | A | 4/1994 | Kiser | 435/14 |
| 5,307,263 | A | 4/1994 | Brown | 600/301 |
| 5,312,590 | A | 5/1994 | Gunasingham | 422/56 |

| Patent | Date | Name | Class |
|---|---|---|---|
| 5,314,441 A | 5/1994 | Cusack | 606/182 |
| 5,314,442 A | 5/1994 | Susumu | 606/182 |
| 5,315,793 A | 5/1994 | Peterson | 451/2 |
| 5,316,012 A | 5/1994 | Siegal | 128/744 |
| 5,318,583 A | 6/1994 | Rabenau | 606/182 |
| 5,318,584 A | 6/1994 | Lange | 606/182 |
| 5,320,607 A | 6/1994 | Ishibashi | 604/115 |
| 5,320,808 A | 6/1994 | Holen | 422/64 |
| 5,324,302 A | 6/1994 | Crouse | 606/181 |
| 5,324,303 A | 6/1994 | Strong | 606/181 |
| 5,330,634 A | 7/1994 | Wong | 205/777.5 |
| 5,332,479 A | 7/1994 | Uenoyama | 204/153.12 |
| 5,341,206 A | 8/1994 | Pittaro | 356/301 |
| 5,342,382 A | 8/1994 | Brinkerhoff | 606/184 |
| 5,344,703 A | 9/1994 | Kovar | 428/312.6 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,365,699 A | 11/1994 | Armstrong | 451/7 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki | 600/578 |
| 5,370,509 A | 12/1994 | Golding | 417/423.1 |
| 5,371,687 A | 12/1994 | Holmes | 364/514 |
| 5,372,135 A | 12/1994 | Mendelson | 600/322 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentzekow | 435/180 |
| 5,390,450 A | 2/1995 | Goenka | 451/39 |
| 5,393,903 A | 2/1995 | Graetzel | 556/137 |
| 5,395,339 A | 3/1995 | Talonn | 604/111 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,283 A | 4/1995 | Goenka | 451/39 |
| 5,405,510 A | 4/1995 | Betts | 205/782 |
| 5,405,511 A | 4/1995 | White | 204/153.1 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,409,664 A | 4/1995 | Allen | |
| 5,410,059 A | 4/1995 | Fraser | 546/10 |
| 5,415,169 A | 5/1995 | Siczek | 600/427 |
| 5,418,142 A | 5/1995 | Kiser | 435/14 |
| 5,423,847 A | 6/1995 | Strong et al. | 606/182 |
| 5,424,545 A | 6/1995 | Block | 350/343 |
| 5,426,032 A | 6/1995 | Phillips | 435/14 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,453,360 A | 9/1995 | Yu | 435/28 |
| 5,454,828 A | 10/1995 | Schraga | 606/181 |
| 5,456,875 A | 10/1995 | Lambert | 264/328.1 |
| 5,459,325 A | 10/1995 | Hueton | 250/458.1 |
| 5,460,182 A | 10/1995 | Goodman | 600/342 |
| 5,462,533 A | 10/1995 | Daugherty | 604/164 |
| 5,464,418 A | 11/1995 | Schraga | 606/182 |
| 5,465,722 A | 11/1995 | Fort | 600/447 |
| 5,471,102 A | 11/1995 | Becker | 310/50 |
| 5,472,427 A | 12/1995 | Rammler | 604/164.01 |
| 5,474,084 A | 12/1995 | Cunniff | 600/164.01 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| D367,109 S | 2/1996 | Ryner | D24/224 |
| 5,490,505 A | 2/1996 | Diab | 600/323 |
| 5,496,274 A | 3/1996 | Graves | 604/86 |
| 5,496,453 A | 3/1996 | Uenoyama | 205/777.5 |
| 5,498,542 A | 3/1996 | Corey | 435/283.1 |
| 5,501,836 A | 3/1996 | Myerson | 42/57 |
| 5,501,893 A | 3/1996 | Laermer | 428/161 |
| 5,507,288 A | 4/1996 | Bocker | 128/633 |
| 5,507,629 A | 4/1996 | Jarvik | 417/423.3 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith | 606/182 |
| 5,515,170 A | 5/1996 | Matzinger | 356/423 |
| 5,518,006 A | 5/1996 | Mawhirt | 128/770 |
| D371,198 S | 6/1996 | Savage | D24/169 |
| 5,524,636 A | 6/1996 | Sarvazyan | 128/774 |
| 5,525,511 A | 6/1996 | D'Costa | 435/287.9 |
| 5,525,518 A | 6/1996 | Lundsgaard | 436/68 |
| 5,526,120 A | 6/1996 | Jina | 356/446 |
| 5,527,333 A | 6/1996 | Nikkels | 606/182 |
| 5,527,334 A | 6/1996 | Kanner | 606/182 |
| 5,529,074 A | 6/1996 | Greenfield | 600/557 |
| 5,540,676 A | 7/1996 | Freiberg | |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,545,291 A | 8/1996 | Smith | 438/107 |
| 5,547,702 A | 8/1996 | Gleisner | 427/2.13 |
| D373,419 S | 9/1996 | Muramatsu | D24/165 |
| 5,554,153 A | 9/1996 | Costello | 606/9 |
| 5,554,166 A | 9/1996 | Lange | 606/182 |
| 5,558,834 A | 9/1996 | Chu | 422/55 |
| 5,562,384 A | 10/1996 | Alvite | 414/226.01 |
| 5,562,696 A | 10/1996 | Nobles | 606/185 |
| 5,563,031 A | 10/1996 | Yu | 435/4 |
| 5,563,042 A | 10/1996 | Phillips | 435/14 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,591,139 A | 1/1997 | Lin | 604/264 |
| 5,593,852 A | 1/1997 | Heller | 435/14 |
| 5,599,501 A | 2/1997 | Carey | 422/64 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,279 A | 4/1997 | Grenshaw | 204/402 |
| 5,620,863 A | 4/1997 | Tomasco | 435/14 |
| 5,624,458 A | 4/1997 | Lipscher | 606/181 |
| 5,624,459 A | 4/1997 | Kortenbach | 606/185 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Susumu | 606/182 |
| 5,628,890 A | 5/1997 | Carter | 204/403 |
| 5,628,961 A | 5/1997 | Davis | 422/63 |
| 5,630,828 A | 5/1997 | Mawhirt | 606/187 |
| 5,630,986 A | 5/1997 | Charlton | 422/64 |
| 5,632,410 A | 5/1997 | Moulton | 221/79 |
| 5,640,954 A | 6/1997 | Pfeiffer | 128/635 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,660,791 A | 8/1997 | Brenneman | 422/58 |

| Patent No. | Date | Inventor | Class |
|---|---|---|---|
| 5,858,804 A | 8/1997 | Zanzucchi | 506/9 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Henrik-Egesborg | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 411/3 R |
| 5,730,753 A | 3/1998 | Susumu | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Susumu | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons et al. | |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird et al. | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| D403,975 S | 1/1999 | Douglas | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,860,922 A | 1/1999 | Gordon et al. | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Decatur et al. | |
| 5,872,713 A | 2/1999 | Douglas | 702/85 |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roeper | 606/344 |
| 5,880,829 A | 3/1999 | Kauhaniemi | 356/246 |
| 5,882,494 A | 3/1999 | van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,893,848 A | 4/1999 | Negus | 606/41 |
| 5,893,870 A | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat | 606/170 |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D411,619 S | 6/1999 | Duchon | D24/146 |
| 5,316,229 A | 6/1999 | Evans | 606/171 |
| 5,908,416 A | 6/1999 | Costello | 606/169 |
| 5,911,937 A | 6/1999 | Hekal | 264/255 |
| 5,912,134 A | 6/1999 | Shartle | 435/7.24 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |
| RE36,268 E | 8/1999 | Szuminsky | 205/777.5 |
| 5,931,794 A | 8/1999 | Pitesky | 600/556 |
| 5,933,136 A | 8/1999 | Brown | 345/327 |
| 5,935,075 A | 8/1999 | Casscells | 600/474 |
| 5,938,679 A | 8/1999 | Freeman | 606/181 |
| 5,940,153 A | 8/1999 | Castaneda | |

| | | | |
|---|---|---|---|
| 5,942,102 A | 8/1999 | Hodges .................... 205/775 |
| 5,942,189 A | 8/1999 | Wolfbeis ................ 422/82.08 |
| 5,947,957 A | 9/1999 | Morris ........................ 606/13 |
| 5,951,300 A | 9/1999 | Brown ...................... 434/236 |
| 5,951,492 A | 9/1999 | Douglas .................... 600/583 |
| 5,951,493 A | 9/1999 | Douglas et al. ............. 600/583 |
| 5,951,582 A | 9/1999 | Thorne ..................... 606/182 |
| 5,951,836 A | 9/1999 | McAleer .................... 204/403 |
| 5,954,738 A | 9/1999 | LeVaughn ................. 606/181 |
| 5,956,501 A | 9/1999 | Brown ................... 395/500.32 |
| 5,957,846 A | 9/1999 | Chiang ..................... 600/447 |
| 5,958,199 A | 9/1999 | Miyamoto ................. 204/403 |
| 5,959,098 A | 9/1999 | Goldberg .................. 536/25.3 |
| 5,960,403 A | 9/1999 | Brown .......................... 705/2 |
| 5,961,451 A | 10/1999 | Reber ........................ 600/322 |
| 5,964,718 A | 10/1999 | Duchon ..................... 600/583 |
| 5,965,380 A | 10/1999 | Heller .......................... 435/14 |
| 5,968,063 A | 10/1999 | Chu ............................ 606/185 |
| 5,968,760 A | 10/1999 | Phillips ........................ 435/14 |
| 5,968,836 A | 10/1999 | Matzinger ................. 436/169 |
| 5,971,941 A | 10/1999 | Simons ...................... 606/573 |
| 5,972,199 A | 10/1999 | Heller ...................... 205/777.5 |
| 5,972,294 A | 10/1999 | Smith .......................... 422/58 |
| 5,972,715 A | 10/1999 | Celentano ................ 436/164 |
| 5,974,124 A | 10/1999 | Schlueter ............. 379/106.02 |
| 5,976,085 A | 11/1999 | Kimball ...................... 600/309 |
| 5,983,193 A | 11/1999 | Heinonen ...................... 705/2 |
| 5,985,116 A | 11/1999 | Ikeda ........................ 204/403 |
| 5,985,559 A | 11/1999 | Brown ........................... 435/6 |
| 5,986,754 A | 11/1999 | Harding .................... 356/246 |
| 5,993,100 A | 11/1999 | Gastmann ................. 600/595 |
| 5,993,400 A | 11/1999 | Rincoe ....................... 600/595 |
| 5,993,434 A | 11/1999 | Dev ............................. 604/501 |
| D417,504 S | 12/1999 | Love ......................... D24/169 |
| 5,997,476 A | 12/1999 | Brown ...................... 600/300 |
| 5,997,561 A | 12/1999 | Boecker .................... 606/182 |
| 5,997,817 A | 12/1999 | Crismore ..................... 422/58 |
| 5,997,818 A | 12/1999 | Hackner .................... 422/681 |
| 6,001,067 A | 12/1999 | Shults ........................ 600/584 |
| 6,007,497 A | 12/1999 | Huitema ................... 600/567 |
| D418,602 S | 1/2000 | Prokop ..................... D24/169 |
| 6,014,577 A | 1/2000 | Henning .................... 600/345 |
| 6,015,392 A | 1/2000 | Douglas .................... 600/583 |
| 6,018,289 A | 1/2000 | Sekura .................... 340/309.4 |
| 6,020,110 A | 2/2000 | Williams ..................... 430/315 |
| 6,022,324 A | 2/2000 | Skinner .................... 600/566 |
| 6,022,366 A | 2/2000 | Schraga ..................... 606/181 |
| 6,022,748 A | 2/2000 | Charych ................... 436/527 |
| 6,023,629 A | 2/2000 | Tamada ..................... 600/347 |
| 6,023,686 A | 2/2000 | Brown ........................ 705/37 |
| 6,027,459 A | 2/2000 | Shain et al. |
| 6,030,399 A | 2/2000 | Ignotz ........................ 606/167 |
| 6,030,827 A | 2/2000 | Davis ........................ 435/287 |
| 6,030,967 A | 2/2000 | Marui ......................... 514/215 |
| 6,032,059 A | 2/2000 | Henning .................... 600/345 |
| 6,032,119 A | 2/2000 | Brown ........................... 705/2 |
| 6,033,421 A | 3/2000 | Theiss ........................ 606/186 |
| 6,033,866 A | 3/2000 | Guo ............................. 435/14 |
| 6,036,924 A | 3/2000 | Simons ...................... 422/100 |
| 6,037,178 A | 3/2000 | Leiner .......................... 436/50 |
| 6,041,253 A | 3/2000 | Kost .............................. 604/20 |
| 6,045,567 A | 4/2000 | Taylor ....................... 606/181 |
| 6,046,055 A | 4/2000 | Wolfbeis .................... 436/172 |
| 6,048,352 A | 4/2000 | Douglas .................... 606/181 |
| D424,696 S | 5/2000 | Ray .......................... D24/169 |
| 6,056,701 A | 5/2000 | Duchon ..................... 600/583 |
| 6,059,815 A | 5/2000 | Lee ............................ 606/209 |
| 6,060,327 A | 5/2000 | Keen ......................... 436/518 |
| 6,061,128 A | 5/2000 | Zweig ..................... 356/243.4 |
| 6,063,039 A | 5/2000 | Cunningham ............. 600/573 |
| 6,066,103 A | 5/2000 | Duchon ..................... 600/583 |
| 6,066,243 A | 5/2000 | Anderson ................ 422/82.01 |
| 6,066,296 A | 5/2000 | Brady .......................... 422/63 |
| 6,067,463 A | 5/2000 | Jeng .......................... 600/336 |
| 6,068,615 A | 5/2000 | Brown ....................... 604/207 |
| D426,638 S | 6/2000 | Ray .......................... D24/169 |
| 6,070,761 A | 6/2000 | Bloom ......................... 222/81 |
| 6,071,249 A | 6/2000 | Cunningham ............. 600/578 |
| 6,071,250 A | 6/2000 | Douglas .................... 600/583 |
| 6,071,251 A | 6/2000 | Cunningham ............. 600/584 |
| 6,071,294 A | 6/2000 | Simons ...................... 606/181 |
| 6,071,391 A | 6/2000 | Gotoh ........................ 204/403 |
| 6,074,360 A | 6/2000 | Hans-Peter .................. 604/57 |
| 6,077,408 A | 6/2000 | Miyamoto ................. 204/403 |
| 6,080,106 A | 6/2000 | Lloyd ........................ 600/300 |
| 6,080,172 A | 6/2000 | Fujiwara ................... 606/166 |
| D428,150 S | 7/2000 | Ruf ........................... D24/146 |
| 6,083,196 A | 7/2000 | Trautman ..................... 604/46 |
| 6,083,710 A | 7/2000 | Heller .......................... 435/14 |
| 6,084,660 A | 7/2000 | Shartle ........................ 356/39 |
| 6,085,576 A | 7/2000 | Sunshine .................. 73/29.01 |
| 6,086,544 A | 7/2000 | Hibner ....................... 600/568 |
| 6,086,545 A | 7/2000 | Roe ........................... 600/570 |
| 6,086,562 A | 7/2000 | Jacobsen ................... 604/156 |
| 6,090,078 A | 7/2000 | Erskine ...................... 604/198 |
| 6,091,975 A | 7/2000 | Daddona ................... 600/345 |
| 6,093,146 A | 7/2000 | Filangeri ................... 600/300 |
| 6,093,156 A | 7/2000 | Cunningham |
| D428,993 S | 8/2000 | Lubs ......................... D24/165 |
| 6,099,484 A | 8/2000 | Douglas .................... 600/583 |
| 6,099,802 A | 8/2000 | Pugh ............................ 422/58 |
| 6,100,107 A | 8/2000 | Lei ............................... 438/50 |
| 6,101,478 A | 8/2000 | Brown ........................... 705/2 |
| 6,102,933 A | 8/2000 | Lee ............................ 606/209 |
| 6,103,033 A | 8/2000 | Say .......................... 156/73.1 |
| 6,103,509 A | 8/2000 | Sode .......................... 435/190 |
| 6,104,940 A | 8/2000 | Watanabe .................. 600/345 |
| 6,106,751 A | 8/2000 | Talbot .......................... 264/81 |
| 6,107,083 A | 8/2000 | Collins ...................... 435/288 |
| 6,113,578 A | 9/2000 | Brown ....................... 604/207 |
| 6,117,630 A | 9/2000 | Reber ............................ 435/4 |
| 6,118,126 A | 9/2000 | Zanzucchi ............... 250/458.1 |
| 6,119,033 A | 9/2000 | Spigelman ................. 600/426 |
| 6,120,462 A | 9/2000 | Hibner ....................... 600/566 |
| 6,120,676 A | 9/2000 | Heller ...................... 205/777.5 |
| 6,121,009 A | 9/2000 | Heller .......................... 435/14 |
| 6,122,536 A | 9/2000 | Sun ........................... 600/341 |
| 6,126,804 A | 10/2000 | Andresen ................... 204/601 |
| 6,126,899 A | 10/2000 | Woudenberg ............... 422/50 |
| 6,129,823 A | 10/2000 | Hughes ................. 204/403.01 |
| 6,132,449 A | 10/2000 | Lum .......................... 606/181 |
| 6,133,837 A | 10/2000 | Riley ...................... 340/573.1 |
| 6,134,461 A | 10/2000 | Say ............................ 600/345 |
| 6,136,013 A | 10/2000 | Marshall .................... 606/167 |
| 6,139,562 A | 10/2000 | Mauze ....................... 606/171 |
| 6,143,164 A | 11/2000 | Heller ........................ 600/583 |
| 6,144,837 A | 11/2000 | Quy ......................... 434/307 R |
| 6,149,203 A | 11/2000 | Hanlon ......................... 283/72 |
| 6,151,586 A | 11/2000 | Brown ......................... 705/14 |
| 6,152,875 A | 11/2000 | Hakamata .................. 600/319 |
| 6,152,942 A | 11/2000 | Brenneman ............... 606/181 |
| 6,153,069 A | 11/2000 | Pottgen ..................... 204/403 |
| RE36,991 E | 12/2000 | Yamamoto ................. 204/403 |
| 6,155,267 A | 12/2000 | Nelson ........................ 128/899 |
| 6,155,992 A | 12/2000 | Henning et al. ............. 600/583 |
| 6,156,051 A | 12/2000 | Schraga .................... 606/181 |
| 6,157,442 A | 12/2000 | Raskas ......................... 356/39 |
| 6,159,147 A | 12/2000 | Lichter ...................... 600/300 |
| 6,159,424 A | 12/2000 | Kauhaniemi ................. 422/63 |
| 6,161,095 A | 12/2000 | Brown ........................... 705/2 |
| 6,162,397 A | 12/2000 | Jurik ............................ 422/56 |
| 6,162,611 A | 12/2000 | Heller .......................... 435/14 |
| 6,167,362 A | 12/2000 | Brown ......................... 703/11 |
| 6,167,386 A | 12/2000 | Brown ........................ 705/37 |
| 6,168,563 B1 | 1/2001 | Brown ....................... 600/301 |
| 6,168,957 B1 | 1/2001 | Matzinger ................. 436/518 |
| 6,171,325 B1 | 1/2001 | Mauze et al. ................. 606/171 |
| 6,172,743 B1 | 1/2001 | Kley et al. ...................... 356/39 |
| 6,175,752 B1 | 1/2001 | Say ............................ 600/345 |
| 6,176,847 B1 | 1/2001 | Humphreys ................ 604/246 |
| 6,176,865 B1 | 1/2001 | Mauze ....................... 606/171 |
| 6,177,000 B1 | 1/2001 | Peterson ................... 205/777.5 |
| 6,177,931 B1 | 1/2001 | Alexander et al. |
| 6,183,489 B1 | 2/2001 | Douglas .................... 606/181 |
| 6,186,145 B1 | 2/2001 | Brown ....................... 128/897 |
| 6,190,612 B1 | 2/2001 | Berger .................... 422/82.07 |
| 6,191,852 B1 | 2/2001 | Paffhausen ................. 356/244 |
| 6,192,891 B1 | 2/2001 | Gravel ....................... 128/920 |

| Patent No. | Date | Name | Class |
|---|---|---|---|
| 6,193,673 B1 | 2/2001 | Viola | 600/568 |
| 6,193,873 B1 | 2/2001 | Ohara | 205/792 |
| 6,194,900 B1 | 2/2001 | Freeman | 324/321 |
| 6,197,040 B1 | 3/2001 | LeVaughn | 606/182 |
| 6,197,257 B1 | 3/2001 | Raskas | 422/82.05 |
| 6,200,773 B1 | 3/2001 | Ouyang | 435/26 |
| 6,203,504 B1 | 3/2001 | Latterell | 600/576 |
| 6,206,841 B1 | 3/2001 | Cunningham et al. | 600/584 |
| 6,210,133 B1 | 4/2001 | Aboul-Hosn | 417/423.1 |
| 6,210,272 B1 | 4/2001 | Brown | 463/1 |
| 6,210,369 B1 | 4/2001 | Wilmot | 604/157 |
| 6,210,420 B1 | 4/2001 | Mauze | 606/182 |
| 6,210,421 B1 | 4/2001 | Bocker | 606/182 |
| 6,212,417 B1 | 4/2001 | Ikeda | 204/403.14 |
| 6,214,626 B1 | 4/2001 | Meller | 436/165 |
| 6,214,804 B1 | 4/2001 | Felgner | 514/44 |
| 6,218,571 B1 | 4/2001 | Zheng | 562/61 |
| 6,219,574 B1 | 4/2001 | Cormier | 604/20 |
| 6,221,023 B1 | 4/2001 | Matsuba | 600/486 |
| 6,221,238 B1 | 4/2001 | Grundig | 205/777.5 |
| 6,225,078 B1 | 5/2001 | Ikeda | 435/25 |
| 6,228,100 B1 | 5/2001 | Schraga | |
| 6,230,051 B1 | 5/2001 | Cormier | 604/20 |
| 6,230,501 B1 | 5/2001 | Bailey | 62/51.1 |
| 6,231,531 B1 | 5/2001 | Lum | 601/46 |
| 6,233,471 B1 | 5/2001 | Berner | 600/345 |
| 6,233,539 B1 | 5/2001 | Brown | 703/11 |
| 6,234,772 B1 | 5/2001 | Wampler | 417/423.12 |
| 6,238,926 B1 | 5/2001 | Cunningham | 600/573 |
| 6,240,393 B1 | 5/2001 | Brown | 705/1 |
| D444,235 S | 6/2001 | Roberts | D24/169 |
| 6,241,862 B1 | 6/2001 | McAleer | 204/403 |
| 6,242,207 B1 | 6/2001 | Douglas | 435/25 |
| 6,245,060 B1 | 6/2001 | Loomis | 245/6/9 |
| 6,245,215 B1 | 6/2001 | Douglas | 205/775 |
| 6,246,992 B1 | 6/2001 | Brown | 705/2 |
| 6,248,065 B1 | 6/2001 | Brown | 600/300 |
| 6,251,083 B1 | 6/2001 | Yum | 600/584 |
| 6,251,121 B1 | 6/2001 | Saadat | |
| 6,251,260 B1 | 6/2001 | Heller | 205/777.5 |
| 6,251,344 B1 | 6/2001 | Goldstein | 422/123 |
| D444,557 S | 7/2001 | Levaughn | D24/146 |
| 6,254,831 B1 | 7/2001 | Barnard | 422/82.08 |
| 6,256,533 B1 | 7/2001 | Vuzhakov | 604/21 |
| 6,258,111 B1 | 7/2001 | Ross | 606/171 |
| 6,258,229 B1 | 7/2001 | Winarta | 204/403 |
| 6,258,254 B1 | 7/2001 | Miyamoto | 205/777.5 |
| 6,261,241 B1 | 7/2001 | Burbank | 600/564 |
| 6,261,245 B1 | 7/2001 | Kawai | 600/576 |
| 6,261,519 B1 | 7/2001 | Harding | |
| 6,264,635 B1 | 7/2001 | Wampler | 604/151 |
| 6,268,161 B1 | 7/2001 | Han | 435/14 |
| 6,268,162 B1 | 7/2001 | Phillips | 435/14 |
| 6,269,314 B1 | 7/2001 | Iitawaki | 702/23 |
| 6,270,455 B1 | 8/2001 | Brown | 600/300 |
| 6,270,637 B1 | 8/2001 | Crismore | 204/403 |
| 6,272,359 B1 | 8/2001 | Kivela | 455/567 |
| 6,272,364 B1 | 8/2001 | Kurnik | 600/345 |
| 6,275,717 B1 | 8/2001 | Gross | 600/345 |
| 6,280,254 B1 | 8/2001 | Wu | 439/630 |
| 6,281,006 B1 | 8/2001 | Heller | 435/287.9 |
| 6,283,926 B1 | 9/2001 | Cunningham | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas | 356/446 |
| 6,289,254 B1 | 9/2001 | Shimizu | 700/96 |
| 6,290,683 B1 | 9/2001 | Erez | 604/273 |
| 6,294,897 B1 | 9/2001 | Champlin | 320/153 |
| 6,295,506 B1 | 9/2001 | Heinonen | 702/104 |
| 6,299,578 B1 | 10/2001 | Kurnik | 600/309 |
| 6,299,596 B1 | 10/2001 | Ding | 604/96.01 |
| 6,299,757 B1 | 10/2001 | Feldman | 205/775 |
| 6,302,844 B1 | 10/2001 | Walker | 600/300 |
| 6,302,855 B1 | 10/2001 | Lav | 600/584 |
| 6,305,804 B1 | 10/2001 | Rice | 351/221 |
| 6,306,104 B1 | 10/2001 | Cunningham | 600/573 |
| 6,306,152 B1 | 10/2001 | Verdonk | 606/182 |
| 6,306,347 B1 | 10/2001 | Mason | 422/58 |
| 6,309,351 B1 | 10/2001 | Kurnik | 600/309 |
| 6,309,535 B1 | 10/2001 | Williams | 205/777.5 |
| 6,312,612 B1 | 11/2001 | Sherman | 216/2 |
| 6,315,738 B1 | 11/2001 | Nishikawa | |
| 6,318,970 B1 | 11/2001 | Backhouse | 417/92 |
| 6,319,210 B1 | 11/2001 | Douglas | 600/583 |
| 6,322,574 B1 | 11/2001 | Lloyd | 606/181 |
| 6,322,808 B1 | 11/2001 | Trautman | 424/448 |
| 6,322,963 B1 | 11/2001 | Bauer | 435/4 |
| 6,329,161 B1 | 12/2001 | Heller | 435/14 |
| 6,330,426 B2 | 12/2001 | Brown | 434/307 R |
| 6,331,163 B1 | 12/2001 | Kaplan | 600/486 |
| 6,332,871 B1 | 12/2001 | Douglas | 600/583 |
| 6,334,363 B1 | 1/2002 | Testud | 73/862 |
| 6,334,778 B1 | 1/2002 | Brown | 434/258 |
| 6,334,856 B1 | 1/2002 | Allen | 604/191 |
| 6,335,203 B1 | 1/2002 | Patel | 436/169 |
| 6,335,856 B1 | 1/2002 | Allen | 604/191 |
| 6,336,900 B1 | 1/2002 | Alleckson | 600/485 |
| 6,338,790 B1 | 1/2002 | Feldman | 205/777.5 |
| 6,346,120 B1 | 2/2002 | Yamazaki | 623/3.13 |
| 6,349,229 B1 | 2/2002 | Watanabe | 600/345 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas | 600/583 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,364,890 B1 | 4/2002 | Lum | 606/181 |
| 6,368,273 B1 | 4/2002 | Brown | 600/300 |
| 6,375,469 B1 | 4/2002 | Brown | 434/236 |
| 6,375,627 B1 | 4/2002 | Mauze | 600/584 |
| 6,379,301 B1 | 4/2002 | Worthington | 600/309 |
| 6,379,317 B1 | 4/2002 | Kintzig | 600/573 |
| 6,379,324 B1 | 4/2002 | Gartstein | 604/22 |
| 6,379,969 B1 | 4/2002 | Mauze et al. | |
| 6,381,577 B1 | 4/2002 | Brown | 705/2 |
| D456,910 S | 5/2002 | Clark | D24/225 |
| 6,387,709 B1 | 5/2002 | Mason | 436/164 |
| 6,391,005 B1 | 5/2002 | Lum | 604/117 |
| 6,395,227 B1 | 5/2002 | Kiser | 422/56 |
| 6,398,522 B2 | 6/2002 | Skill | 417/410.3 |
| 6,398,562 B1 | 6/2002 | Butler | 439/91 |
| 6,399,394 B1 | 6/2002 | Dahm | 436/180 |
| 6,402,701 B1 | 6/2002 | Kaplan | 600/567 |
| 6,402,704 B1 | 6/2002 | Mcmorrow | 600/576 |
| 6,409,740 B1 | 6/2002 | Kuhr | 606/182 |
| 6,413,410 B1 | 7/2002 | Hodges | 205/775 |
| 6,413,411 B1 | 7/2002 | Pottgen | 205/777.5 |
| 6,415,821 B2 | 7/2002 | Kamholz | 137/827 |
| 6,420,128 B1 | 7/2002 | Ouyang | 435/14 |
| 6,421,633 B1 | 7/2002 | Heinonen | 703/11 |
| 6,423,014 B1 | 7/2002 | Churchill | 600/587 |
| 6,428,664 B1 | 8/2002 | Bhullar | 204/403.03 |
| 6,436,055 B1 | 8/2002 | Roe | 600/584 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,444,115 B1 | 9/2002 | Hodges | 205/792 |
| 6,447,265 B1 | 9/2002 | Antaki | 417/354 |
| 6,451,040 B1 | 9/2002 | Purcell | 606/181 |
| 6,453,810 B1 | 9/2002 | Rossmeisl | 101/123 |
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons | 436/63 |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,745,750 B2 | 11/2002 | Han | 435/14 |
| 6,488,827 B1 | 12/2002 | Shartle | 204/403 |

| Patent No. | Kind | Date | Name | Class |
|---|---|---|---|---|
| 6,488,891 | B2 | 12/2002 | Mason | 422/58 |
| 6,489,052 | B1 | 12/2002 | Acker | 600/584 |
| 6,489,133 | B2 | 12/2002 | Phillips | 435/14 |
| 6,491,709 | B2 | 12/2002 | Sharma | 606/181 |
| 6,491,870 | B2 | 12/2002 | Patel | 422/58 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,501,976 | B1 | 12/2002 | Sohrab | 600/347 |
| 6,503,210 | B1 | 1/2003 | Hirao | 600/576 |
| 6,503,231 | B1 | 1/2003 | Prausnitz | 604/272 |
| 6,503,290 | B1 | 1/2003 | Hakky et al. | |
| 6,503,381 | B1 | 1/2003 | Gotoh | 204/403.14 |
| 6,506,165 | B1 | 1/2003 | Sweeney | 600/562 |
| 6,506,168 | B1 | 1/2003 | Fathallah | 600/578 |
| 6,506,575 | B1 | 1/2003 | Knappe | 435/14 |
| 6,508,795 | B1 | 1/2003 | Samuelsson et al. | 604/113 |
| 6,512,986 | B1 | 1/2003 | Harmon | 702/84 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |
| 6,521,110 | B1 | 2/2003 | Hodges | 204/403.14 |
| 6,521,182 | B1 | 2/2003 | Shartle | 422/58 |
| 6,527,521 | B2 | 3/2003 | Noda | 417/355 |
| 6,527,716 | B1 | 3/2003 | Eppstein | 600/309 |
| 6,527,778 | B2 | 3/2003 | Athanasiou | 606/80 |
| 6,529,377 | B1 | 3/2003 | Nelson | 361/699 |
| 6,530,892 | B1 | 3/2003 | Kelly | 600/583 |
| 6,530,937 | B1 | 3/2003 | Schraga | 606/182 |
| 6,531,322 | B1 | 3/2003 | Jurik | 436/95 |
| 6,533,949 | B1 | 3/2003 | Yeshurun | 216/11 |
| 6,537,207 | B1 | 3/2003 | Rice | 600/121 |
| 6,537,242 | B1 | 3/2003 | Palmer | 604/22 |
| 6,537,292 | B1 | 3/2003 | Lee | 606/182 |
| 6,540,672 | B1 | 4/2003 | Simonsen | 600/300 |
| 6,540,675 | B2 | 4/2003 | Aceti | 600/309 |
| 6,540,762 | B1 | 4/2003 | Bertling | 606/182 |
| 6,540,891 | B1 | 4/2003 | Stewart | 204/403.14 |
| 6,541,266 | B2 | 4/2003 | Modzelewski | 436/95 |
| 6,547,954 | B2 | 4/2003 | Ikeda | 205/777.5 |
| 6,549,796 | B2 | 4/2003 | Sohrab | 600/345 |
| 6,551,494 | B1 | 4/2003 | Heller | 205/777.5 |
| 6,553,244 | B2 | 4/2003 | Lesho | 600/583 |
| 6,554,381 | B2 | 4/2003 | Locher | 347/7 |
| 6,555,061 | B1 | 4/2003 | Leong | 422/58 |
| D475,136 | S | 5/2003 | Taniguchi | D24/165 |
| 6,558,320 | B1 | 5/2003 | Causey | 600/300 |
| 6,558,361 | B1 | 5/2003 | Yeshurun | 604/272 |
| 6,558,402 | B1 | 5/2003 | Chelak | 606/182 |
| 6,558,528 | B1 | 5/2003 | Matzinger | 205/777.5 |
| 6,560,471 | B1 | 5/2003 | Heller | 600/347 |
| 6,561,978 | B1 | 5/2003 | Conn | 600/309 |
| 6,561,989 | B2 | 5/2003 | Whitson | 600/573 |
| 6,562,210 | B1 | 5/2003 | Bhullar | 204/403.3 |
| 6,565,509 | B1 | 5/2003 | Say | 600/365 |
| 6,565,808 | B2 | 5/2003 | Hudak | 422/58 |
| 6,569,157 | B1 | 5/2003 | Shain | 606/12 |
| 6,571,651 | B1 | 6/2003 | Hodges | 73/864.72 |
| 6,572,566 | B2 | 6/2003 | Effenhauser | 600/584 |
| 6,572,822 | B2 | 6/2003 | Jurik | 422/56 |
| 6,574,490 | B2 | 6/2003 | Abbink | 600/316 |
| 6,575,905 | B2 | 6/2003 | Knobbe | 600/365 |
| 6,576,101 | B1 | 6/2003 | Heller | 204/403.14 |
| 6,576,117 | B1 | 6/2003 | Kazuo | 205/777.5 |
| 6,576,416 | B2 | 6/2003 | Haviland | 435/4 |
| 6,579,690 | B1 | 6/2003 | Bonnecaze et al. | 435/14 |
| 6,582,573 | B2 | 6/2003 | Douglas | 204/403.1 |
| 6,584,338 | B1 | 6/2003 | Van Muiswinkel | 600/419 |
| D477,670 | S | 7/2003 | Jurik | D24/225 |
| 6,586,199 | B2 | 7/2003 | Ouyang | 435/26 |
| 6,587,705 | B1 | 7/2003 | Kim | 600/347 |
| 6,589,260 | B1 | 7/2003 | Schmelzeisen-R | 606/181 |
| 6,589,261 | B1 | 7/2003 | Abulhaj | 606/181 |
| 6,591,124 | B2 | 7/2003 | Sherman | 600/345 |
| 6,591,125 | B1 | 7/2003 | Buse | 600/347 |
| 6,592,744 | B1 | 7/2003 | Hodges | 205/775 |
| 6,592,745 | B1 | 7/2003 | Feldman | 205/777.5 |
| 6,595,919 | B2 | 7/2003 | Berner | 600/365 |
| 6,599,407 | B2 | 7/2003 | Taniike | 204/403.1 |
| 6,599,693 | B1 | 7/2003 | Webb | 435/4 |
| 6,599,769 | B2 | 7/2003 | Kondo | 438/28 |
| 6,601,534 | B2 | 8/2003 | Hebrank | 119/6.8 |
| 6,602,205 | B1 | 8/2003 | Erickson | 600/573 |
| 6,602,268 | B2 | 8/2003 | Kuhr | 606/181 |
| 6,602,678 | B2 | 8/2003 | Kwon | 435/14 |
| 6,604,050 | B2 | 8/2003 | Trippel | 702/19 |
| 6,607,362 | B2 | 8/2003 | Lum | 417/53 |
| 6,607,494 | B1 | 8/2003 | Fowler | 600/570 |
| 6,607,658 | B1 | 8/2003 | Heller | 205/777.5 |
| 6,612,111 | B1 | 9/2003 | Hodges | 60/593 |
| 6,616,616 | B2 | 9/2003 | Fritz | 600/583 |
| 6,616,819 | B1 | 9/2003 | Liamos | 204/403.02 |
| 6,618,934 | B1 | 9/2003 | Feldman | 29/830 |
| 6,620,112 | B2 | 9/2003 | Klitmose | 600/583 |
| 6,620,310 | B1 | 9/2003 | Ohara | 205/792 |
| 6,623,501 | B2 | 9/2003 | Heller | 606/181 |
| 6,626,851 | B2 | 9/2003 | Hirao | 600/576 |
| 6,632,349 | B1 | 10/2003 | Hodges | 205/792 |
| 6,635,222 | B2 | 10/2003 | Kent | 422/22 |
| 6,638,415 | B1 | 10/2003 | Hodges | 205/775 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beatty | 205/792 |
| 6,649,416 | B1 | 11/2003 | Kauer | 436/164 |
| 6,650,915 | B2 | 11/2003 | Routt | 600/319 |
| 6,652,720 | B1 | 11/2003 | Mansouri | 204/403.13 |
| 6,652,734 | B1 | 11/2003 | Hodges | 205/777.5 |
| 6,652,814 | B1 | 11/2003 | House | 422/104 |
| D484,600 | S | 12/2003 | Kaar | D24/169 |
| 6,656,697 | B1 | 12/2003 | Ouyang | 435/7.9 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,662,439 | B1 | 12/2003 | Bhullar | 29/825 |
| 6,669,669 | B2 | 12/2003 | Flaherty | 604/132 |
| 6,671,527 | B2 | 12/2003 | Petersson | 600/316 |
| D484,980 | S | 1/2004 | Hartwein | D24/165 |
| 6,673,617 | B2 | 1/2004 | Patel | 436/8 |
| 6,676,995 | B2 | 1/2004 | Dick | 427/286 |
| 6,679,841 | B2 | 1/2004 | Bojan | 600/309 |
| 6,679,852 | B1 | 1/2004 | Schmelzeisen | 600/583 |
| 6,682,933 | B2 | 1/2004 | Patel | 436/8 |
| 6,689,411 | B2 | 2/2004 | Dick | 427/2.13 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa | 264/403.09 |
| 6,709,692 | B2 | 3/2004 | Sudor | 427/2.1 |
| 6,713,660 | B1 | 3/2004 | Roe | 604/361 |
| 6,716,577 | B1 | 4/2004 | Yu | 435/6 |
| 6,719,887 | B2 | 4/2004 | Hasegawa | 204/403.09 |
| 6,719,923 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui et al. | 204/403.01 |
| 6,730,494 | B1 | 5/2004 | Toranto | 435/28 |
| 6,731,966 | B1 | 5/2004 | Spigelman | 600/407 |
| 6,733,493 | B2 | 5/2004 | Gruzdev | 606/9 |
| 6,736,777 | B2 | 5/2004 | Kim | 600/365 |
| 6,738,654 | B2 | 5/2004 | Sohrab | 600/345 |
| 6,740,215 | B1 | 5/2004 | Yamamoto | 204/403.14 |
| 6,743,211 | B1 | 6/2004 | PraUSnitz | 604/239 |
| 6,743,597 | B1 | 6/2004 | Guo | 435/14 |
| 6,743,635 | B2 | 6/2004 | Neel | 436/95 |
| 6,746,872 | B2 | 6/2004 | Zheng | 436/16 |
| 6,749,618 | B2 | 6/2004 | Levaughn | 606/182 |
| 6,749,740 | B2 | 6/2004 | Liamos | 205/792 |
| 6,749,792 | B2 | 6/2004 | Olsen | 264/328.1 |
| 6,749,887 | B1 | 6/2004 | Dick | 427/2.13 |
| 6,751,491 | B2 | 6/2004 | Lew | 600/345 |
| 6,752,817 | B2 | 6/2004 | Flora | 606/181 |
| 6,753,187 | B2 | 6/2004 | Cizdziel | 436/169 |

| Patent No. | Kind | Date | Name | Class |
|---|---|---|---|---|
| 6,759,190 | B2 | 7/2004 | Lin | 435/4 |
| 6,764,496 | B2 | 7/2004 | Schraga | 606/182 |
| 6,764,581 | B1 | 7/2004 | Forrow | 204/403 |
| 6,767,441 | B1 | 7/2004 | Cai | 204/403.03 |
| 6,773,671 | B1 | 8/2004 | Lewis | 422/58 |
| 6,776,888 | B2 | 8/2004 | Yamamoto | 204/403.06 |
| 6,780,645 | B2 | 8/2004 | Hayter | 436/8 |
| 6,780,647 | B2 | 8/2004 | Fujiwara | 436/169 |
| 6,783,502 | B2 | 8/2004 | Orloff | 600/583 |
| 6,783,537 | B1 | 8/2004 | Kuhr | 606/182 |
| 6,784,274 | B2 | 8/2004 | van Antwerp | 528/77 |
| 6,786,874 | B2 | 9/2004 | Grace | 600/573 |
| 6,787,013 | B2 | 9/2004 | Chang | 204/412 |
| 6,787,109 | B2 | 9/2004 | Haar | 422/82.05 |
| 6,790,327 | B2 | 9/2004 | Ikeda | 204/403.1 |
| 6,790,599 | B1 | 9/2004 | Madou | 430/320 |
| 6,792,791 | B2 | 9/2004 | Sato | 73/1.02 |
| 6,793,632 | B2 | 9/2004 | Sohrab | 600/573 |
| 6,793,633 | B2 | 9/2004 | Douglas | 600/583 |
| 6,793,802 | B2 | 9/2004 | Lee | 205/777.5 |
| 6,797,150 | B2 | 9/2004 | Kermani | 205/777.5 |
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |
| 6,805,780 | B1 | 10/2004 | Ryu | 204/403.01 |
| 6,808,499 | B1 | 10/2004 | Churchill | 600/587 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,406 | B2 | 11/2004 | Grubge | |
| 6,811,557 | B1 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.1 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |
| 6,816,742 | B2 | 11/2004 | Kim | 600/345 |
| 6,818,180 | B2 | 11/2004 | Douglas | 422/58 |
| 6,821,483 | B2 | 11/2004 | Phillips | 422/58 |
| 6,823,750 | B2 | 11/2004 | Hodges | 73/864.72 |
| 6,825,047 | B1 | 11/2004 | Woudenberg | 436/518 |
| 6,827,250 | B2 | 12/2004 | Uhland | 228/110.1 |
| 6,827,829 | B2 | 12/2004 | Kawanaka | 204/403.02 |
| 6,829,507 | B1* | 12/2004 | Lidman et al. | 607/19 |
| 6,830,551 | B1 | 12/2004 | Uchigaki | 600/584 |
| 6,830,668 | B2 | 12/2004 | Musho | 204/400 |
| 6,830,669 | B2 | 12/2004 | Miyazaki | 204/409 |
| 6,830,934 | B1 | 12/2004 | Hardling | 436/166 |
| 6,833,540 | B2 | 12/2004 | MacKenzie | 250/214 |
| 6,835,184 | B1 | 12/2004 | Sage | 604/46 |
| 6,835,553 | B2 | 12/2004 | Han | 435/14 |
| 6,835,570 | B2 | 12/2004 | Patel | 436/8 |
| 6,837,858 | B2 | 1/2005 | Cunningham | 600/573 |
| 6,837,976 | B2 | 1/2005 | Cai | 204/403.14 |
| 6,837,988 | B2 | 1/2005 | Leong | 205/792 |
| 6,840,912 | B2 | 1/2005 | Kloepfer | 600/573 |
| 6,841,052 | B2 | 1/2005 | Musho | 204/401 |
| 6,843,254 | B2 | 1/2005 | Tapper | 128/898 |
| 6,843,902 | B1 | 1/2005 | Penner | 205/76 |
| 6,847,451 | B2 | 1/2005 | Pugh | 356/436 |
| 6,849,052 | B2 | 2/2005 | Uchigaki et al. | |
| 6,849,168 | B2 | 2/2005 | Crumly | 204/416 |
| 6,849,216 | B2 | 2/2005 | Rappin | 264/134 |
| 6,849,456 | B2 | 2/2005 | Patel | 436/8 |
| 6,850,790 | B2 | 2/2005 | Berner | 600/347 |
| 6,852,119 | B1 | 2/2005 | Abulhaj | 606/182 |
| 6,852,212 | B2 | 2/2005 | Maxwell | 205/775 |
| 6,852,500 | B1 | 2/2005 | Hoss | 435/14 |
| 6,853,854 | B1 | 2/2005 | Proniewiez | 600/319 |
| 6,855,243 | B2 | 2/2005 | Khan | 205/777.5 |
| 6,856,125 | B2 | 2/2005 | Kermani | 324/71.1 |
| 6,856,928 | B2 | 2/2005 | Harmon | 702/84 |
| 6,858,015 | B2 | 2/2005 | List | 600/583 |
| 6,858,401 | B2 | 2/2005 | Phillips | 435/14 |
| 6,859,738 | B2 | 2/2005 | Bush | 702/25 |
| 6,862,466 | B2 | 3/2005 | Ackerman | 600/347 |
| 6,862,534 | B2 | 3/2005 | Sterling | 702/23 |
| 6,863,800 | B2 | 3/2005 | Karinka | 205/777.5 |
| 6,863,801 | B2 | 3/2005 | Hodges | 205/792 |
| 6,865,408 | B1 | 3/2005 | Abbink | 600/310 |
| 6,866,641 | B2 | 3/2005 | Marshall | 600/583 |
| 6,866,675 | B2 | 3/2005 | Perez | 606/181 |
| 6,866,758 | B2 | 3/2005 | Bhullar | 204/403.2 |
| 6,866,822 | B1 | 3/2005 | House | 422/82.05 |
| 6,869,418 | B2 | 3/2005 | Marano-Ford | 604/192 |
| 6,872,200 | B2 | 3/2005 | Mann | 604/890.1 |
| 6,872,297 | B2 | 3/2005 | Mansouri | 205/775 |
| 6,872,298 | B2 | 3/2005 | Kermani | 205/777.5 |
| 6,872,299 | B2 | 3/2005 | Kermani | 205/777.5 |
| 6,872,358 | B2 | 3/2005 | Hagen | 422/61 |
| 6,875,208 | B2 | 4/2005 | Santini | 604/890.1 |
| 6,875,223 | B2 | 4/2005 | Argauer | 606/181 |
| 6,875,327 | B1 | 4/2005 | Miyazaki | 204/403.14 |
| 6,875,613 | B2 | 4/2005 | Shartle | 436/63 |
| 6,878,120 | B2 | 4/2005 | Roe | 600/583 |
| 6,878,251 | B2 | 4/2005 | Hodges | 204/403.14 |
| 6,878,255 | B1 | 4/2005 | Wang | 204/452 |
| 6,878,262 | B2 | 4/2005 | Taniike | 205/777.5 |
| 6,880,968 | B1 | 4/2005 | Haar | 374/131 |
| 6,881,203 | B2 | 4/2005 | Delmore | 604/272 |
| 6,881,322 | B2 | 4/2005 | Tokunaga | 205/775 |
| 6,881,378 | B1 | 4/2005 | Zimmer | 422/58 |
| 6,881,541 | B2 | 4/2005 | Petersen et al. | |
| 6,881,550 | B2 | 4/2005 | Phillips | 435/14 |
| 6,881,551 | B2 | 4/2005 | Heller | 435/14 |
| 6,881,578 | B2 | 4/2005 | Otake | 436/44 |
| 6,882,940 | B2 | 4/2005 | Potts | 702/23 |
| 6,884,592 | B2 | 4/2005 | Matzinger | 435/7.1 |
| 6,885,196 | B2 | 4/2005 | Taniike | 324/444 |
| 6,885,883 | B2 | 4/2005 | Parris | 600/347 |
| 6,887,202 | B2 | 5/2005 | Currie | 600/309 |
| 6,887,239 | B2 | 5/2005 | Elstrom | 606/41 |
| 6,887,253 | B2 | 5/2005 | Curie | 606/181 |
| 6,887,426 | B2 | 5/2005 | Phillips | 422/56 |
| 6,887,709 | B2 | 5/2005 | Leong | 436/8 |
| 6,889,069 | B2 | 5/2005 | Routt | 600/319 |
| 6,890,319 | B1 | 5/2005 | Crocker | 604/131 |
| 6,890,421 | B2 | 5/2005 | Ohara | 205/777.5 |
| 6,890,484 | B2 | 5/2005 | Bautista | 422/58 |
| 6,891,936 | B2 | 5/2005 | Kai | 379/106.02 |
| 6,892,085 | B2 | 5/2005 | McIvor | 600/347 |
| 6,893,396 | B2 | 5/2005 | Schulze | 600/300 |
| 6,893,545 | B2 | 5/2005 | Gotoh | 204/403.5 |
| 6,893,552 | B1 | 5/2005 | Wang | 205/777.5 |
| 6,895,263 | B2 | 5/2005 | Shin | 600/316 |
| 6,895,264 | B2 | 5/2005 | Rice | 600/319 |
| 6,895,265 | B2 | 5/2005 | Silver | 600/345 |
| 6,896,793 | B2 | 5/2005 | Erdosy | 205/775 |
| 6,897,788 | B2 | 5/2005 | Khair | 340/870.16 |
| 6,902,905 | B2 | 6/2005 | Burson | 435/14 |
| 6,904,301 | B2 | 6/2005 | Raskas | 600/310 |
| 6,905,733 | B2 | 6/2005 | Russell | 427/393.5 |
| 6,908,008 | B2 | 6/2005 | Pugh | 221/135 |
| 6,908,535 | B2 | 6/2005 | Rankin | 204/406 |
| 6,908,591 | B2 | 6/2005 | MacPhee | 422/22 |
| 6,908,593 | B1 | 6/2005 | Shartle | 422/58 |
| 6,911,130 | B2 | 6/2005 | Brenneman | 204/400 |
| 6,911,131 | B2 | 6/2005 | Miyazaki | 204/403.14 |
| 6,911,621 | B2 | 6/2005 | Bhullar | 219/121.69 |
| 6,911,937 | B1 | 6/2005 | Sparrow | 342/188 |
| 6,913,210 | B2 | 7/2005 | Baasch | 239/407 |
| 6,913,668 | B2 | 7/2005 | Matzinger | 156/256 |
| 6,916,410 | B2 | 7/2005 | Katsuki | 204/403 |
| 6,918,901 | B1 | 7/2005 | Theeuwes et al. | |
| 6,918,918 | B1 | 7/2005 | Schraga | 606/182 |
| 6,922,576 | B2 | 7/2005 | Raskas | 600/316 |
| 6,922,578 | B2 | 7/2005 | Eppstein | 600/347 |
| 6,923,764 | B2 | 8/2005 | Aceti | 600/309 |
| 6,923,894 | B2 | 8/2005 | Huang | 204/403.06 |
| 6,923,936 | B2 | 8/2005 | Swanson | 422/22 |
| 6,924,093 | B2 | 8/2005 | Haviland | 435/4 |
| 6,925,317 | B1 | 8/2005 | Samuels | 600/344 |

| Patent | Date | Name | Class |
|---|---|---|---|
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.04 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/365 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D522,656 S | 6/2006 | Orr | D24/169 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,059,352 B2 | 6/2006 | Bohm | 137/828 |
| 7,060,059 B2 | 6/2006 | Keith | 604/504 |
| 7,060,168 B2 | 6/2006 | Taniike | 204/403.04 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,079,252 B1 | 7/2006 | Debreezeny | 356/451 |

| Patent No. | Date | Name | Ref |
|---|---|---|---|
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Schraga | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,113,172 B2 | 9/2006 | Hohl | 345/168 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/364 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/182 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,799 B2 | 2/2007 | Berner | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Kasai | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erikson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman et al. | |
| 7,226,414 B2 | 6/2007 | Ballerstadt | 600/365 |
| 7,226,461 B2 | 6/2007 | Boecker et al. | |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Freeman | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 2,747,138 A1 | 7/2007 | Reghabi | 600/365 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,251,573 B2 | 7/2007 | Kondoh | 600/310 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |

| Patent No. | Date | Name | Class |
|---|---|---|---|
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen-Redeker | 606/181 |
| 7,291,256 B2 | 11/2007 | Teodorczyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,320,412 B2 | 1/2008 | Mann | 340/870.07 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.01 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Schartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,720 B2 | 5/2008 | Azarnia | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/777.5 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |

| Patent/Publication | Date | Inventor | Class |
|---|---|---|---|
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0031931 A1 | 10/2001 | Cunningham | 600/573 |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016606 A1 | 2/2002 | Moerman | 606/181 |
| 2002/0016923 A1 | 2/2002 | Knaus | 713/200 |
| 2002/0019606 A1 | 2/2002 | Lebel | 604/66 |
| 2002/0019747 A1 | 2/2002 | Ware | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Paul et al. | |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan et al. | |
| 2002/0103499 A1 | 8/2002 | Perez | 606/182 |
| 2002/0120216 A1 | 8/2002 | Fritz | 600/583 |
| 2002/0120261 A1 | 8/2002 | Morris | 606/41 |
| 2002/0123335 A1 | 9/2002 | Luna | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1* | 4/2003 | Boecker et al. | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | |
| 2003/0111357 A1 | 6/2003 | Black | 205/775 |
| 2003/0113827 A1 | 6/2003 | Burkoth | 435/14 |
| 2003/0116447 A1 | 6/2003 | Surridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman et al. | |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191376 A1 | 10/2003 | Samuels | 600/309 |
| 2003/0191415 A1 | 10/2003 | Moerman | 13/600 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0210811 A1 | 11/2003 | Dubowsky | 382/128 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |

| | | | | | | | |
|---|---|---|---|---|---|---|---|
| 2003/0233055 A1 | 12/2003 | Erickson | 600/573 | 2004/0162573 A1 | 8/2004 | Keheiri | 606/182 |
| 2003/0233112 A1 | 12/2003 | Alden et al. | 606/181 | 2004/0167383 A1 | 8/2004 | Kim | 600/365 |
| 2003/0233113 A1 | 12/2003 | Alden et al. | 606/182 | 2004/0171057 A1 | 9/2004 | Yang | 435/6 |
| 2004/0006285 A1 | 1/2004 | Douglas | 600/583 | 2004/0171968 A1 | 9/2004 | Katsuki | 600/583 |
| 2004/0007585 A1 | 1/2004 | Griffith | 221/232 | 2004/0172000 A1 | 9/2004 | Roe | 604/361 |
| 2004/0009100 A1 | 1/2004 | Simons | 422/102 | 2004/0173472 A1 | 9/2004 | Jung | 205/777.5 |
| 2004/0010279 A1 | 1/2004 | Freeman | 606/182 | 2004/0173488 A1 | 9/2004 | Griffin | 206/363 |
| 2004/0015064 A1 | 1/2004 | Parsons | 600/347 | 2004/0176705 A1 | 9/2004 | Stevens | 600/584 |
| 2004/0019250 A1 | 1/2004 | Catelli | 600/1 | 2004/0176732 A1 | 9/2004 | Frazier | 604/345 |
| 2004/0019259 A1 | 1/2004 | Brown | 600/300 | 2004/0178066 A1 | 9/2004 | Miyazaki | 204/403.01 |
| 2004/0023858 A1 | 2/2004 | Forrow | 204/403 | 2004/0178067 A1 | 9/2004 | Miyazaki | 204/403.1 |
| 2004/0026243 A1 | 2/2004 | Davies | 204/403.14 | 2004/0178216 A1 | 9/2004 | Brickwood | 221/268 |
| 2004/0026244 A1 | 2/2004 | Hodges | 204/409 | 2004/0180379 A1 | 9/2004 | van Duyne | 435/7.1 |
| 2004/0030353 A1 | 2/2004 | Schmelzeisen-R | 606/201 | 2004/0182703 A1 | 9/2004 | Bell | 204/403.11 |
| 2004/0031682 A1 | 2/2004 | Wilsey | 204/403.1 | 2004/0185568 A1 | 9/2004 | Matsumoto | 436/8 |
| 2004/0034318 A1 | 2/2004 | Fritz | 604/19 | 2004/0186359 A1 | 9/2004 | Beaudoin | 600/310 |
| 2004/0038045 A1 | 2/2004 | Smart | 428/446 | 2004/0186394 A1 | 9/2004 | Roe | 600/598 |
| 2004/0039303 A1 | 2/2004 | Wurster | 600/584 | 2004/0186500 A1 | 9/2004 | Koilke | 606/181 |
| 2004/0039342 A1 | 2/2004 | Eppstein | 604/200 | 2004/0193201 A1 | 9/2004 | Kim | 606/181 |
| 2004/0039407 A1 | 2/2004 | Schraga | 606/181 | 2004/0193377 A1 | 9/2004 | Brown | 702/1 |
| 2004/0039408 A1 | 2/2004 | Abulhaj | 606/181 | 2004/0194302 A1 | 10/2004 | Bhullar | 29/847 |
| 2004/0049219 A1 | 3/2004 | Briggs | 606/181 | 2004/0197231 A1 | 10/2004 | Katsuki | 422/68.1 |
| 2004/0049220 A1 | 3/2004 | Boecker | 606/181 | 2004/0197821 A1 | 10/2004 | Bauer | 437/7.1 |
| 2004/0050694 A1 | 3/2004 | Yang | 204/403.02 | 2004/0199062 A1 | 10/2004 | Petersson | 600/316 |
| 2004/0054267 A1 | 3/2004 | Feldman | 204/316 | 2004/0199069 A1 | 10/2004 | Brown | 705/3 |
| 2004/0054898 A1 | 3/2004 | Heller | 205/777.5 | 2004/0200409 A1 | 10/2004 | Musho | 204/403.01 |
| 2004/0059256 A1 | 3/2004 | Perez | 600/583 | 2004/0200720 A1 | 10/2004 | Bhullar | 204/403.01 |
| 2004/0060818 A1 | 4/2004 | Feldman | 204/403.01 | 2004/0200721 A1 | 10/2004 | Aceti | 422/82.05 |
| 2004/0061841 A1 | 4/2004 | Black | 355/30 | 2004/0202576 A1 | 10/2004 | Perez | 600/583 |
| 2004/0064068 A1 | 4/2004 | DeNuzzio | 600/583 | 2004/0204662 A1 | 10/2004 | Bhullar | 204/403.1 |
| 2004/0069657 A1 | 4/2004 | Hodges | 205/787 | 2004/0206625 A1 | 10/2004 | Hodges | 205/792 |
| 2004/0087990 A1 | 5/2004 | Boecker | 606/181 | 2004/0206636 A1 | 10/2004 | Hammerstedt | 206/524.1 |
| 2004/0092842 A1 | 5/2004 | Boecker | 600/575 | 2004/0206658 A1 | 10/2004 | Valkirs | 435/7.1 |
| 2004/0092994 A1 | 5/2004 | Briggs | 606/181 | 2004/0209307 A1 | 10/2004 | Sakata | 435/287.1 |
| 2004/0092995 A1 | 5/2004 | Boecker | 606/181 | 2004/0209350 A1 | 10/2004 | Mathies | 435/287.2 |
| 2004/0096991 A1 | 5/2004 | Zhang | 436/518 | 2004/0209354 A1 | 10/2004 | Gruzdev | 607/89 |
| 2004/0098009 A1 | 5/2004 | Boecker | 606/181 | 2004/0210279 A1 | 10/2004 | Pamidi | 204/403.01 |
| 2004/0098010 A1 | 5/2004 | Davison | 606/181 | 2004/0211666 A1 | 10/2004 | Paek | 435/7.92 |
| 2004/0102803 A1 | 5/2004 | Boecker | 606/183 | 2004/0214253 A1 | 10/2004 | Sakata | 606/181 |
| 2004/0106855 A1 | 6/2004 | Brown | 600/301 | 2004/0215224 A1 | 10/2004 | Nakayama | 606/182 |
| 2004/0106858 A1 | 6/2004 | Say | 600/345 | 2004/0215225 A1 | 10/2004 | Sato | 73/64.56 |
| 2004/0106859 A1 | 6/2004 | Say | 600/345 | 2004/0216516 A1 | 11/2004 | Cai | 205/792 |
| 2004/0106860 A1 | 6/2004 | Say | 600/345 | 2004/0217019 A1 | 11/2004 | Brown | 434/307 R |
| 2004/0106904 A1 | 6/2004 | Gonnelli | 604/173 | 2004/0219500 A1 | 11/2004 | Bell | 435/6 |
| 2004/0106941 A1 | 6/2004 | Roe | 606/181 | 2004/0219535 A1 | 11/2004 | Eppstein | 600/309 |
| 2004/0107116 A1 | 6/2004 | Brown | 705/2 | 2004/0220456 A1 | 11/2004 | Cahir | 600/562 |
| 2004/0115754 A1 | 6/2004 | Chang | 435/14 | 2004/0220495 A1 | 11/2004 | Ho | 606/47 |
| 2004/0115831 A1 | 6/2004 | Meathrel | 436/514 | 2004/0220564 A1 | 11/2004 | Rutynowski | 606/181 |
| 2004/0116780 A1 | 6/2004 | Brown | 600/300 | 2004/0220603 A1 | 11/2004 | Musho | 204/401 |
| 2004/0116829 A1 | 6/2004 | Raney | 600/573 | 2004/0222092 A1 | 11/2004 | Cai | 435/7.7 |
| 2004/0117207 A1 | 6/2004 | Brown | 705/2 | 2004/0224369 A1 | 11/2004 | Liamos | 600/583 |
| 2004/0117208 A1 | 6/2004 | Brown | 705/2 | 2004/0225230 A1 | 11/2004 | Levaughn | 606/181 |
| 2004/0117209 A1 | 6/2004 | Brown | 705/2 | 2004/0225311 A1 | 11/2004 | Orloff | 606/182 |
| 2004/0117210 A1 | 6/2004 | Brown | 705/2 | 2004/0225312 A1 | 11/2004 | Levaughn | 606/181 |
| 2004/0122339 A1 | 6/2004 | Roe | | 2004/0230216 A1 | 11/2004 | Shen | 204/403.01 |
| 2004/0127818 A1 | 7/2004 | Roe | 600/583 | 2004/0231983 A1 | 11/2004 | Lauks | 204/416 |
| 2004/0127819 A1 | 7/2004 | Roe | 600/583 | 2004/0231984 A1 | 11/2004 | Okuda | 205/789 |
| 2004/0127928 A1 | 7/2004 | Whitson | 606/181 | 2004/0232009 A1 | 11/2004 | Hodges | 600/583 |
| 2004/0127929 A1 | 7/2004 | Roe | 606/181 | 2004/0236250 A1 | 11/2004 | Roe | 600/583 |
| 2004/0132167 A1 | 7/2004 | Rule | 435/287.1 | 2004/0236251 A1 | 11/2004 | Mitragotri | 604/20 |
| 2004/0133125 A1 | 7/2004 | Miyashita | 600/573 | 2004/0236268 A1 | 11/2004 | Schraga | 606/181 |
| 2004/0133127 A1 | 7/2004 | Roe | 600/583 | 2004/0236362 A1 | 11/2004 | Bhullar | 204/400 |
| 2004/0137640 A1 | 7/2004 | Hirao | 436/514 | 2004/0238357 A1 | 12/2004 | Forrow | 204/403 |
| 2004/0138541 A1 | 7/2004 | Ward | 600/345 | 2004/0238358 A1 | 12/2004 | Ikeda | 204/403.1 |
| 2004/0138588 A1 | 7/2004 | Saikley | 600/583 | 2004/0238359 A1 | 12/2004 | Adlassnig | 435/7.1 |
| 2004/0138688 A1 | 7/2004 | Giraud | 606/181 | 2004/0241746 A1 | 12/2004 | Dosmann | 600/315 |
| 2004/0146958 A1 | 7/2004 | Bae | 435/14 | 2004/0242977 A1 | 12/2004 | D'Agostino | 606/181 |
| 2004/0154932 A1 | 8/2004 | Deng | 205/777.5 | 2004/0243164 A1 | 12/2004 | Koike | 606/181 |
| 2004/0157017 A1 | 8/2004 | Mauze | 428/35.7 | 2004/0243165 A1 | 12/2004 | Willner | 204/403 |
| 2004/0157149 A1 | 8/2004 | Hofmann | 430/131 | 2004/0245101 A1 | 12/2004 | Sobha | 435/287.2 |
| 2004/0157319 A1 | 8/2004 | Keen | 435/287.2 | 2004/0248282 A1 | 12/2004 | Vreeke | 436/95 |
| 2004/0157338 A1 | 8/2004 | Burke | 436/147 | 2004/0248312 A1 | 12/2004 | Racchini | 600/347 |
| 2004/0157339 A1 | 8/2004 | Burke | 436/149 | 2004/0249310 A1 | 12/2004 | Shartle | 600/583 |
| 2004/0158137 A1 | 8/2004 | Eppstein | 600/347 | 2004/0249311 A1 | 12/2004 | Haar | 600/584 |
| 2004/0158271 A1 | 8/2004 | Hamamoto | 606/181 | 2004/0249405 A1 | 12/2004 | Watanabe | 606/181 |
| 2004/0161737 A1 | 8/2004 | Yang | 435/5 | 2004/0249406 A1 | 12/2004 | Griffin | 606/182 |
| 2004/0162473 A1 | 8/2004 | Sohrab | 600/345 | 2004/0251131 A1 | 12/2004 | Ueno | 204/403 |
| 2004/0162474 A1 | 8/2004 | Kiser | 600/345 | 2004/0253634 A1 | 12/2004 | Wang | 435/7.1 |
| 2004/0162506 A1 | 8/2004 | Duchon | 600/583 | 2004/0254434 A1 | 12/2004 | Goodnow | 600/365 |

| Pub. No. | Date | Name | Class |
|---|---|---|---|
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Katsuji | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0149090 A1 | 7/2005 | Morita | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |

| Pub. No. | Date | Name | Class |
|---|---|---|---|
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 436/554 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Day | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.1 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034228 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong et al. | |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |

| Pub. No. | Date | Name | Class |
|---|---|---|---|
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/583 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/842 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0279431 A1 | 10/2006 | Bakarania | 340/870.02 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0266644 A1 | 11/2006 | Pugh | 204/400 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0281187 A1 | 12/2006 | Emery | 436/169 |
| 2006/0282109 A1 | 12/2006 | Jansen | |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman et al. | |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Chen | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |

| Publication No. | Date | Name | Class |
|---|---|---|---|
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0129618 A1 | 6/2007 | Goldberger | 600/345 |
| 2007/0129650 A1 | 6/2007 | Freeman et al. | |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Deshmukh et al. | |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Deshmukh et al. | |
| 2007/0173742 A1 | 7/2007 | Deshmukh | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 606/583 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss | 606/182 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker et al. | |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282176 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |

| Pub. No. | Date | Name | Class |
|---|---|---|---|
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen-R | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee et al. | |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/775 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/317 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214918 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 422/777.5 |
| 2008/0277294 A1 | 11/2008 | Heller | 205/777.5 |
| 2008/0286149 A1 | 11/2008 | Roe | 422/58 |
| 2008/0294068 A1 | 11/2008 | Briggs | 600/583 |
| 2008/0300614 A1 | 12/2008 | Freeman | 606/181 |
| 2008/0318193 A1 | 12/2008 | Alvarez-Icaza | 434/262 |
| 2008/0319284 A1 | 12/2008 | Alvarez-Icaza | 600/309 |
| 2008/0319291 A1 | 12/2008 | Freeman | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman | 600/309 |
| 2009/0026075 A1 | 1/2009 | Harding | 204/403.14 |
| 2009/0026091 A1 | 1/2009 | Harding | 205/777.5 |
| 2009/0027040 A1 | 1/2009 | Kermani | 324/123 |
| 2009/0029479 A1 | 1/2009 | Docherty | 436/149 |
| 2009/0030441 A1 | 1/2009 | Hoerauf | 600/583 |
| 2009/0043177 A1 | 2/2009 | Milledge | 600/309 |
| 2009/0043183 A1 | 2/2009 | Kermani | 600/365 |
| 2009/0048536 A1 | 2/2009 | Freeman | 600/583 |
| 2009/0054813 A1 | 2/2009 | Freeman | 600/584 |
| 2009/0057146 A1 | 3/2009 | Teodorezyk | 204/403.01 |
| 2009/0069716 A1 | 3/2009 | Freeman | 600/583 |
| 2009/0084687 A1 | 4/2009 | Chatelier | 205/792 |
| 2009/0105572 A1 | 4/2009 | Malecha | 600/365 |
| 2009/0105573 A1 | 4/2009 | Malecha | 600/365 |
| 2009/0112123 A1 | 4/2009 | Freeman | 600/583 |

| | | | | |
|---|---|---|---|---|
| 2009/0112155 A1 | 4/2009 | Zhao ............................ 604/67 | EP | 0662367 A1 | 7/1995 |
| 2009/0112180 A1 | 4/2009 | Krulevitch .................. 604/506 | EP | 0359831 | 8/1995 |
| 2009/0112185 A1 | 4/2009 | Krulevitch .................. 604/523 | EP | 0471986 | 10/1995 |
| 2009/0124932 A1 | 5/2009 | Freeman ...................... 606/181 | EP | 0368474 | 12/1995 |
| 2009/0131829 A1 | 5/2009 | Freeman ...................... 600/583 | EP | 0461601 | 12/1995 |
| 2009/0131830 A1 | 5/2009 | Freeman ...................... 600/583 | EP | 0429076 | 1/1996 |
| 2009/0131964 A1 | 5/2009 | Freeman ...................... 606/181 | EP | 0552223 | 7/1996 |
| 2009/0131965 A1 | 5/2009 | Freeman ...................... 606/181 | EP | 0735363 | 10/1996 |
| 2009/0137930 A1 | 5/2009 | Freeman ...................... 600/583 | EP | 0505504 | 3/1997 |
| 2009/0138032 A1 | 5/2009 | Freeman ...................... 606/181 | EP | 0406304 | 8/1997 |
| 2009/0139300 A1 | 6/2009 | Pugh ............................ 73/1.36 | EP | 0537761 | 8/1997 |
| 2009/0184004 A1 | 7/2009 | Chatelier .................... 205/777.5 | EP | 0795601 | 9/1997 |
| 2009/0187351 A1 | 7/2009 | Orr ................................ 702/19 | EP | 0562370 | 11/1997 |
| 2009/0192410 A1 | 7/2009 | Freeman ...................... 600/583 | EP | 0415393 | 12/1997 |
| 2009/0192411 A1 | 7/2009 | Freeman ...................... 600/583 | EP | 0823239 | 2/1998 |
| 2009/0196580 A1 | 8/2009 | Freeman ...................... 386/124 | EP | 0560336 | 5/1998 |
| 2009/0204025 A1 | 8/2009 | Marsot ......................... 600/573 | EP | 0878 708 | 11/1998 |
| 2009/0216100 A1 | 8/2009 | Ebner .......................... 600/347 | EP | 0505475 | 3/1999 |
| 2009/0237262 A1 | 9/2009 | Smith .......................... 340/634 | EP | 0898936 A2 | 3/1999 |
| 2009/0240127 A1 | 9/2009 | Pinaki ......................... 600/365 | EP | 0901018 | 3/1999 |
| 2009/0247838 A1 | 10/2009 | Cummings ................... 600/309 | EP | 0470649 | 6/1999 |
| 2009/0247982 A1 | 10/2009 | Krulevitch .................. 604/500 | EP | 0 951 939 | 10/1999 |
| 2009/0259146 A1 | 10/2009 | Freeman ...................... 600/583 | EP | 0951939 A2 | 10/1999 |
| 2009/0280551 A1 | 11/2009 | Cardosi ....................... 435/190 | EP | 0847447 | 11/1999 |
| 2009/0281457 A1 | 11/2009 | Faulkner ...................... 600/583 | EP | 0964059 | 12/1999 |
| 2009/0281458 A1 | 11/2009 | Faulkner ...................... 600/583 | EP | 0964060 | 12/1999 |
| 2009/0281459 A1 | 11/2009 | Faulkner ...................... 600/583 | EP | 0969097 | 1/2000 |
| 2009/0301899 A1 | 12/2009 | Hodges ....................... 205/777.5 | EP | 0985376 A1 | 3/2000 |
| 2009/0302872 A1 | 12/2009 | Haggett ....................... 324/715 | EP | 0 985 376 | 5/2000 |
| 2009/0302873 A1 | 12/2009 | Haggett ....................... 324/724 | EP | 1021950 | 7/2000 |
| 2009/0322630 A1 | 12/2009 | Friman ........................ 343/720 | EP | 0894869 | 2/2001 |
| 2009/0325307 A1 | 12/2009 | Haggett ....................... 436/150 | EP | 1074832 | 2/2001 |
| 2010/0016700 A1 | 1/2010 | Sieh ............................. 600/365 | EP | 1093854 | 4/2001 |
| 2010/0018878 A1 | 1/2010 | Davies ........................ 205/782 | EP | 1 101 443 | 5/2001 |
| 2010/0030110 A1 | 2/2010 | Choi ............................ 600/583 | EP | 1101443 | 5/2001 |
| 2010/0041084 A1 | 2/2010 | Stephens ...................... 435/14 | EP | 1101443 A2 | 5/2001 |
| | | | EP | 1114995 | 7/2001 |
| | FOREIGN PATENT DOCUMENTS | | EP | 0736607 | 8/2001 |
| DE | 3538313 A1 | 4/1986 | EP | 1 157 660 | 11/2001 |
| DE | 4212315 A1 | 10/1993 | EP | 0874984 | 11/2001 |
| DE | 4320347 | 12/1994 | EP | 1157660 | 11/2001 |
| DE | 4344452 | 6/1995 | EP | 0730037 | 12/2001 |
| DE | 4420232 | 12/1995 | EP | 0636879 | 1/2002 |
| DE | 29800611 U | 7/1998 | EP | 01174083 | 1/2002 |
| DE | 19819407 | 11/1999 | EP | 0851224 | 3/2002 |
| DE | 200 09 475 | 9/2000 | EP | 0759553 | 5/2002 |
| DE | 20009475 | 10/2000 | EP | 0856586 | 5/2002 |
| DE | 29824204 | 10/2000 | EP | 0817809 | 7/2002 |
| DE | 10032042 | 1/2002 | EP | 0872728 | 7/2002 |
| DE | 10057832 | 2/2002 | EP | 0795748 | 8/2002 |
| DE | 10057832 C1 | 2/2002 | EP | 0685737 | 9/2002 |
| DE | 10142232 | 3/2003 | EP | 0958495 | 11/2002 |
| DE | 10208575 C1 | 8/2003 | EP | 0937249 | 12/2002 |
| DE | 10245721 | 12/2003 | EP | 1337182 | 8/2003 |
| DE | 10361560 A1 | 7/2005 | EP | 0880692 | 1/2004 |
| EP | 0112498 A2 | 7/1984 | EP | 01374770 | 1/2004 |
| EP | 137975 A2 | 4/1985 | EP | 1404232 | 4/2004 |
| EP | 0160768 | 11/1985 | EP | 1404233 | 4/2004 |
| EP | 0199484 A2 | 10/1986 | EP | 1246688 | 5/2004 |
| EP | 0254246 | 1/1988 | EP | 1502614 | 2/2005 |
| EP | 0289 269 | 11/1988 | EP | 1643908 | 4/2006 |
| EP | 0317847 A1 | 5/1989 | EP | 1790288 | 5/2007 |
| EP | 0320109 | 6/1989 | EP | 1921992 | 5/2008 |
| EP | 0364208 A1 | 4/1990 | EP | 2039294 | 3/2009 |
| EP | 0170375 | 5/1990 | FR | 2 555 432 A | 5/1985 |
| EP | 0136362 | 12/1990 | FR | 2555432 | 5/1985 |
| EP | 0449525 | 10/1991 | FR | 2622457 | 11/1987 |
| EP | 0453283 | 10/1991 | GB | 1558111 | 12/1979 |
| EP | 0263948 | 2/1992 | GB | 2168815 | 6/1986 |
| EP | 0449147 A2 | 8/1992 | GB | 233936 A | 6/1999 |
| EP | 0530994 | 3/1993 | GB | 2331936 | 6/1999 |
| EP | 0374355 | 6/1993 | GB | 2335860 | 10/1999 |
| EP | 0351891 | 9/1993 | GB | 2335860 A | 10/1999 |
| EP | 0593096 | 4/1994 | GB | 2335990 | 10/1999 |
| EP | 0630609 A2 | 12/1994 | GB | 2335990 A | 10/1999 |
| EP | 0415388 | 5/1995 | JP | HEI 4 194660 | 7/1992 |
| EP | 0654659 | 5/1995 | JP | 1996010208 | 12/1992 |
| EP | 0777123 | 6/1995 | JP | 9-276235 | 10/1997 |
| EP | 0505494 | 7/1995 | JP | 1014906 | 1/1998 |

| | | | | | | |
|---|---|---|---|---|---|---|
| JP | 2000-116768 | 4/2000 | | WO | WO 00/39914 | 7/2000 |
| WO | WO 80/01389 | 7/1980 | | WO | WO 00/42422 | 7/2000 |
| WO | WO 85/04089 | 9/1985 | | WO | WO 00/44084 | 7/2000 |
| WO | WO 86/07632 | 12/1985 | | WO | WO 00/46854 | 8/2000 |
| WO | WO86/005966 | 10/1986 | | WO | WO 00/50771 | 8/2000 |
| WO | WO 91/09139 | 6/1991 | | WO | WO 00/55915 | 9/2000 |
| WO | WO92/03099 | 3/1992 | | WO | WO 00/60340 | 10/2000 |
| WO | WO92/06971 | 4/1992 | | WO | WO 00/64022 | 10/2000 |
| WO | WO92/07263 | 4/1992 | | WO | WO 00/67245 | 11/2000 |
| WO | WO92/07468 | 5/1992 | | WO | WO 00/67268 | 11/2000 |
| WO | WO93/00044 | 1/1993 | | WO | WO 00/72452 | 11/2000 |
| WO | WO 93/02720 | 2/1993 | | WO | WO 01/00090 | 1/2001 |
| WO | WO 93/06979 | 4/1993 | | WO | WO 01/7220 A1 | 2/2001 |
| WO | WO93/09723 | 5/1993 | | WO | WO 01/15807 | 3/2001 |
| WO | WO 93/12726 | 7/1993 | | WO | WO 01/15807 A1 | 3/2001 |
| WO | WO 93/25898 | 12/1993 | | WO | WO 01/16578 A1 | 3/2001 |
| WO | WO 94/27140 | 11/1994 | | WO | WO 01/75433 | 3/2001 |
| WO | WO 94/29703 | 12/1994 | | WO | WO 01/23885 | 4/2001 |
| WO | WO 94/29704 | 12/1994 | | WO | WO 01/25775 | 4/2001 |
| WO | WO 94/29731 | 12/1994 | | WO | WO 01/26813 | 4/2001 |
| WO | WO 95/00662 | 1/1995 | | WO | WO 01/29037 | 4/2001 |
| WO | WO 95/06240 | 3/1995 | | WO | WO 01/33216 | 5/2001 |
| WO | WO 95/10223 | 4/1995 | | WO | WO 01/34029 | 5/2001 |
| WO | WO95/12583 | 5/1995 | | WO | WO 01/36955 | 5/2001 |
| WO | WO 95/22597 | 8/1995 | | WO | WO 01/37174 | 5/2001 |
| WO | WO96/14799 | 5/1996 | | WO | WO 01/45014 A1 | 6/2001 |
| WO | WO 96/30431 | 10/1996 | | WO | WO 01/40788 | 7/2001 |
| WO | WO96/37148 | 11/1996 | | WO | WO 01/57510 | 8/2001 |
| WO | WO 97/02359 | 1/1997 | | WO | WO 01/63271 | 8/2001 |
| WO | WO 97/02487 | 1/1997 | | WO | WO 01/64105 | 9/2001 |
| WO | WO 97/11883 | 4/1997 | | WO | WO 01/66010 | 9/2001 |
| WO | WO 97/11883 A1 | 4/1997 | | WO | WO 01/69505 | 9/2001 |
| WO | WO 97/18464 | 5/1997 | | WO | WO 01/72220 A | 10/2001 |
| WO | WO97/28741 | 8/1997 | | WO | WO 01/72225 | 10/2001 |
| WO | WO 97/30344 | 8/1997 | | WO | WO 01/73124 | 10/2001 |
| WO | WO98/14436 | 8/1997 | | WO | WO 01/73395 | 10/2001 |
| WO | WO 97/42882 | 11/1997 | | WO | WO 01/89691 | 11/2001 |
| WO | WO 97/42888 | 11/1997 | | WO | WO 01/95806 | 12/2001 |
| WO | WO 97/45720 | 12/1997 | | WO | WO 02/00101 | 1/2002 |
| WO | WO 98/03431 | 1/1998 | | WO | WO 02/02796 | 1/2002 |
| WO | WO 98/19159 | 5/1998 | | WO | WO 02/08750 | 1/2002 |
| WO | WO98/19609 | 5/1998 | | WO | WO 02/08753 | 1/2002 |
| WO | WO 98/20332 | 5/1998 | | WO | WO 02/08950 | 1/2002 |
| WO | WO 98/20348 | 5/1998 | | WO | WO 02/18940 | 3/2002 |
| WO | WO98/20867 | 5/1998 | | WO | WO 02/21317 | 3/2002 |
| WO | WO 98/24366 | 6/1998 | | WO | WO 02/25551 | 3/2002 |
| WO | WO 98/24373 | 6/1998 | | WO | WO 02/32559 | 4/2002 |
| WO | WO 98/35225 | 8/1998 | | WO | WO 02/41227 | 5/2002 |
| WO | WO98/45276 | 10/1998 | | WO | WO 02/41779 | 5/2002 |
| WO | WO 99/03584 | 1/1999 | | WO | WO 02/44948 | 6/2002 |
| WO | WO 99/05966 | 2/1999 | | WO | WO 02/49507 | 6/2002 |
| WO | WO99/07295 | 2/1999 | | WO | WO/0249507 | 6/2002 |
| WO | WO 99/07431 | 2/1999 | | WO | WO 02/056769 | 7/2002 |
| WO | WO 99/07431 A1 | 2/1999 | | WO | WO 02/059734 | 8/2002 |
| WO | WO 99/13100 | 3/1999 | | WO | WO 02/069791 | 9/2002 |
| WO | WO 99/62576 | 3/1999 | | WO | WO 02/077638 | 10/2002 |
| WO | WO 99/17854 | 4/1999 | | WO | WO 02/100251 | 12/2002 |
| WO | WO 99/18532 | 4/1999 | | WO | WO 02/100252 | 12/2002 |
| WO | WO 99/19507 | 4/1999 | | WO | WO 02/100253 | 12/2002 |
| WO | WO 99/19717 | 4/1999 | | WO | WO 02/100254 | 12/2002 |
| WO | WO 99/27483 | 6/1999 | | WO | WO 02/100460 | 12/2002 |
| WO | WO 99/27852 | 6/1999 | | WO | WO 02/100461 | 12/2002 |
| WO | WO 99/13100 | 12/1999 | | WO | WO 02/101343 | 12/2002 |
| WO | WO 99/62576 | 12/1999 | | WO | WO 02/101359 | 12/2002 |
| WO | WO 99/64580 | 12/1999 | | WO | WO 03/000321 | 1/2003 |
| WO | WO 00/06024 | 2/2000 | | WO | WO 03/023389 | 3/2003 |
| WO | WO 00/09184 | 2/2000 | | WO | WO 03/042691 | 5/2003 |
| WO | WO 00/11578 | 3/2000 | | WO | WO 03039369 A | 5/2003 |
| WO | WO 00/15103 | 3/2000 | | WO | WO 03/045557 | 6/2003 |
| WO | WO 00/17799 | 3/2000 | | WO | WO 03/046542 | 6/2003 |
| WO | WO 00/17800 | 3/2000 | | WO | WO 03/049609 | 6/2003 |
| WO | WO 00/18293 | 4/2000 | | WO | WO 03/050534 | 6/2003 |
| WO | WO 00/19346 | 4/2000 | | WO | WO 03/066128 | 8/2003 |
| WO | WO 00/20626 | 4/2000 | | WO | WO 03/070099 | 8/2003 |
| WO | WO 00/29577 | 5/2000 | | WO | WO 03/071940 | 9/2003 |
| WO | WO 00/30186 | 5/2000 | | WO | WO 03/082091 | 10/2003 |
| WO | WO 00/32097 | 6/2000 | | WO | WO 03/082091 A2 | 10/2003 |
| WO | WO 00/32098 | 6/2000 | | WO | WO 03/088824 | 10/2003 |
| WO | WO 00/33236 | 6/2000 | | WO | WO 03/088834 | 10/2003 |

| | | |  | | | |
|---|---|---|---|---|---|---|
| WO | WO 03/088835 | 10/2003 | | WO | WO 2005/035017 | 4/2005 |
| WO | WO 03/088851 A1 | 10/2003 | | WO | WO 2005/035018 | 4/2005 |
| WO | WO/03088834 | 10/2003 | | WO | WO 2005/037095 | 4/2005 |
| WO | WO 03/094752 | 11/2003 | | WO | WO 2005/046477 | 5/2005 |
| WO | WO 03/101297 | 12/2003 | | WO | WO 2005/065399 | 7/2005 |
| WO | WO 2004/008130 | 1/2004 | | WO | WO 2005/065414 | 7/2005 |
| WO | WO 2004/022133 | 3/2004 | | WO | WO 2005/065415 | 7/2005 |
| WO | WO 2004/026130 | 4/2004 | | WO | WO 2005065545 A2 | 7/2005 |
| WO | WO 2004/040285 A2 | 5/2004 | | WO | WO 2005/072604 | 8/2005 |
| WO | WO 2004/040287 A1 | 5/2004 | | WO | WO 2005/084546 A2 | 9/2005 |
| WO | WO 2004/040948 | 5/2004 | | WO | WO 2005/084557 | 9/2005 |
| WO | WO 2004/041082 | 5/2004 | | WO | WO 2005/104948 | 11/2005 |
| WO | WO 2004/045375 | 6/2004 | | WO | WO 2005/114185 | 12/2005 |
| WO | WO 2004/054455 | 7/2004 | | WO | WO 2005/116622 | 12/2005 |
| WO | WO 2004/060174 | 7/2004 | | WO | WO 2005/119234 | 12/2005 |
| WO | WO 2004/060446 | 7/2004 | | WO | WO 2005/120197 | 12/2005 |
| WO | WO 2004/091693 | 10/2004 | | WO | WO 2005/120199 | 12/2005 |
| WO | WO 2004/098405 | 11/2004 | | WO | WO 2005/120365 | 12/2005 |
| WO | WO 2004/003147 | 12/2004 | | WO | WO 2005/121759 | 12/2005 |
| WO | WO 2004/107964 | 12/2004 | | WO | WO 2006/001797 | 1/2006 |
| WO | WO 2004/107975 | 12/2004 | | WO | WO 2006/001973 | 1/2006 |
| WO | WO 2004/112602 | 12/2004 | | WO | WO 2006/011062 | 2/2006 |
| WO | WO 2004/112612 | 12/2004 | | WO | WO 2006/013045 | 2/2006 |
| WO | WO 2005/001418 | 1/2005 | | WO | WO 2006/015615 | 2/2006 |
| WO | WO 2005/006939 | 1/2005 | | WO | WO 2006/027702 A2 | 3/2006 |
| WO | WO 2005/011774 | 2/2005 | | WO | WO 2006/031920 | 3/2006 |
| WO | WO 2005/013824 | 2/2005 | | WO | WO 2006/032391 | 3/2006 |
| WO | WO 2005/016125 | 2/2005 | | WO | WO 2006/072004 | 7/2006 |
| WO | WO 2005/018425 | 3/2005 | | WO | WO 2006/105146 | 10/2006 |
| WO | WO 2005/018430 | 3/2005 | | WO | WO 2006/116441 | 11/2006 |
| WO | WO 2005/018454 | 3/2005 | | WO | WO 2007/025635 | 3/2007 |
| WO | WO 2005/018709 | 3/2005 | | WO | WO 2007/044834 | 4/2007 |
| WO | WO 2005/018710 | 3/2005 | | WO | WO 2007/054335 | 5/2007 |
| WO | WO 2005/018711 | 3/2005 | | WO | WO 2007/070719 | 6/2007 |
| WO | WO 2005/022143 | 3/2005 | | WO | WO 2007/084367 | 7/2007 |
| WO | WO 2005/023088 | 3/2005 | | WO | WO 2007/106470 | 9/2007 |
| WO | WO 2005/033659 | 4/2005 | | WO | WO 2007/119900 | 10/2007 |
| WO | WO 2005/034720 | 4/2005 | | WO | WO 2008/112268 | 9/2008 |
| WO | WO 2005/034721 | 4/2005 | | WO | WO 2008/112279 | 9/2008 |
| WO | WO 2005/034741 | 4/2005 | | | | |
| WO | WO 2005/034778 | 4/2005 | | | | |

* cited by examiner

US 7,909,775 B2

METHOD AND APPARATUS FOR LANCET LAUNCHING DEVICE INTEGRATED ONTO A BLOOD-SAMPLING CARTRIDGE

CROSS-REFERENCE TO RELATED APPLICATIONS

This application is a divisional of U.S. Ser. No. 10/363,510 filed Sep. 29, 2003 now U.S. Pat. No. 7,749,174, which is a §3.71 filing of PCT/US02/19060 filed Jun. 12, 2002, which in turn claims the benefit of U.S. Ser. No. 60/297,860 filed, Jun. 12, 2001. All applications above are fully incorporated herein by reference.

TECHNICAL FIELD

Lancing devices are well known in the medical health-care products industry for piercing the skin to produce blood for analysis. Biochemical analysis of blood samples is a diagnostic tool for determining clinical information. Many point-of-care tests are performed using capillary whole blood, the most common being monitoring blood glucose level in diabetics. Typically, a drop of blood is obtained by making a small incision in the fingertip, creating a small wound, which generates a small blood droplet on the surface of the skin.

BACKGROUND ART

Early methods of lancing included piercing or slicing the skin with a needle or razor. Current methods utilize lancet drivers that contain a multitude of spring, cam and mass actuators to drive the lancet. These include cantilever springs, diaphragms, coil springs, as well as gravity plumbs to actuate the lancet. Typically, the device is pre-cocked, or the user cocks the device. The device is held against the skin and the user mechanically triggers the ballistic launch of the lancet.

The problem with current devices is that they require two hands to operate, one to hold the device and push a button which activates the device, and the other hand to provide a finger for lancing. After lancing, the finger needs to be free to move to another device for collection of the blood droplet and subsequent analysis.

Generally, known methods of blood sampling require several steps. First, a measurement session is set up by gathering various paraphernalia such as lancets, launchers, test strips, instrument, etc. Second, the patient must assemble the paraphernalia by loading a sterile lancet, loading a test strip, and arming the launcher.

Third, the patient must place their finger against the lancet launcher and using the other hand activate the launcher. Fourth, the patient must put down the launcher and place the bleeding finger against a test strip, which may or may not have been loaded into the instrument. The patient must insure blood has been loaded onto the test strip and the instrument has been calibrated prior to such loading. Finally, the patient must dispose of all the blood contaminated paraphernalia including the lancet. What has been needed is a blood sampling device and method that simplifies the blood sampling procedure.

DISCLOSURE OF INVENTION

Embodiments of the present invention are related to medical health-care products and to methods for obtaining blood for chemical analysis. More particularly, embodiments of the invention relate to devices and methods for piercing the skin (lancing) with a sensor to detect the presence of a patient's finger and activate the lancet automatically. In some embodiments, the cartridge and lancet are disposable.

In accordance with embodiments of the invention, a patient will be able to obtain a sample of blood in an ergonomic, convenient way using a method and apparatus which integrates lancing, sample collection, and analysis. The presence of patients finger on the ergonomic sampling area is sensed by monitoring the pressure applied by the finger on the cartridge which houses the lancet. The application of a predetermined pressure is measured by a piezoelectric or electrical circuit.

Advantages can be achieved in a blood sampling device by integrating the lancing and blood sample collection procedure so that the device can capture and transport the capillary blood from the wound created by the lancet to a desired active area, such as a strip for analyzing glucose. This can be done in embodiments of the invention by integrating the lancet, conduit and reservoir into a disposable cartridge which can be inserted into a hand-held sampling device with instrumentation for analyzing the blood sample.

In the use of an embodiment of the invention, a finger is placed over an ergonomically contoured sampling area and pressure is applied with the finger so that a sensor will activate the lancet, which will, in turn, lance the finger and allow the blood sample to be collected in the conduit and transported to the reservoir for analysis in a single step from the patients perspective.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Reference will now be made to embodiments of the invention, examples of which are illustrated in the accompanying drawings. Wherever possible, the same reference numbers will be used throughout the drawings to refer to the same or like parts.

Figure 1:
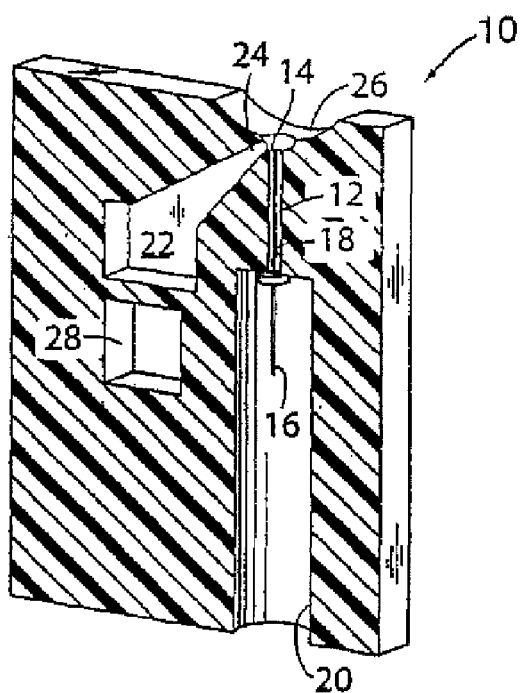
FIG. 1 is a drawing of the cartridge which houses the lancet.

FIG. 1 shows the disposable cartridge (10) which houses the lancet (12).

Disposable means that the cartridge is used for one lancing cycle and is then discarded.

The lancet (12) has a distal end (16) which connects to the driver (40) and a proximal end (14) which lances the skin. The proximal end (14) is embedded within the conduit (18). Embedded means completely shielded by the cartridge when it is not lancing. The distal end (16) extends into the cavity (20). The reservoir (22) has a narrow opening (24) on the ergonomically contoured surface (26) which is adjacent to the proximal end (14) of the lancet (12). The term ergonomically contoured is generally defined to mean shaped to snugly fit a finger placed on the surface. The term reservoir is generally defined to mean an area which allows pooling of the blood sample. The term narrow is generally defined to mean a reduction in diameter of the reservoir so as to exploit capillary forces to better channel the blood into the rest of the reservoir. The term adjacent, as used in the context of the proximity of the proximal end (16) and narrow opening (24), is generally defined to mean that the proximal end (16) and the narrow opening (24) are located in the same general area. The cartridge (10) is capable of channeling the blood sample, which means transporting through small passages (not shown), to an active area (28) which corresponds to the device's system for analyzing the blood. This system can consist of a chemical, physical, optical, electrical or other means of analyzing the blood sample. The lancet and reservoir embodiment illustrated are integrated into the cartridge in a single packaged unit.

Figure 2:
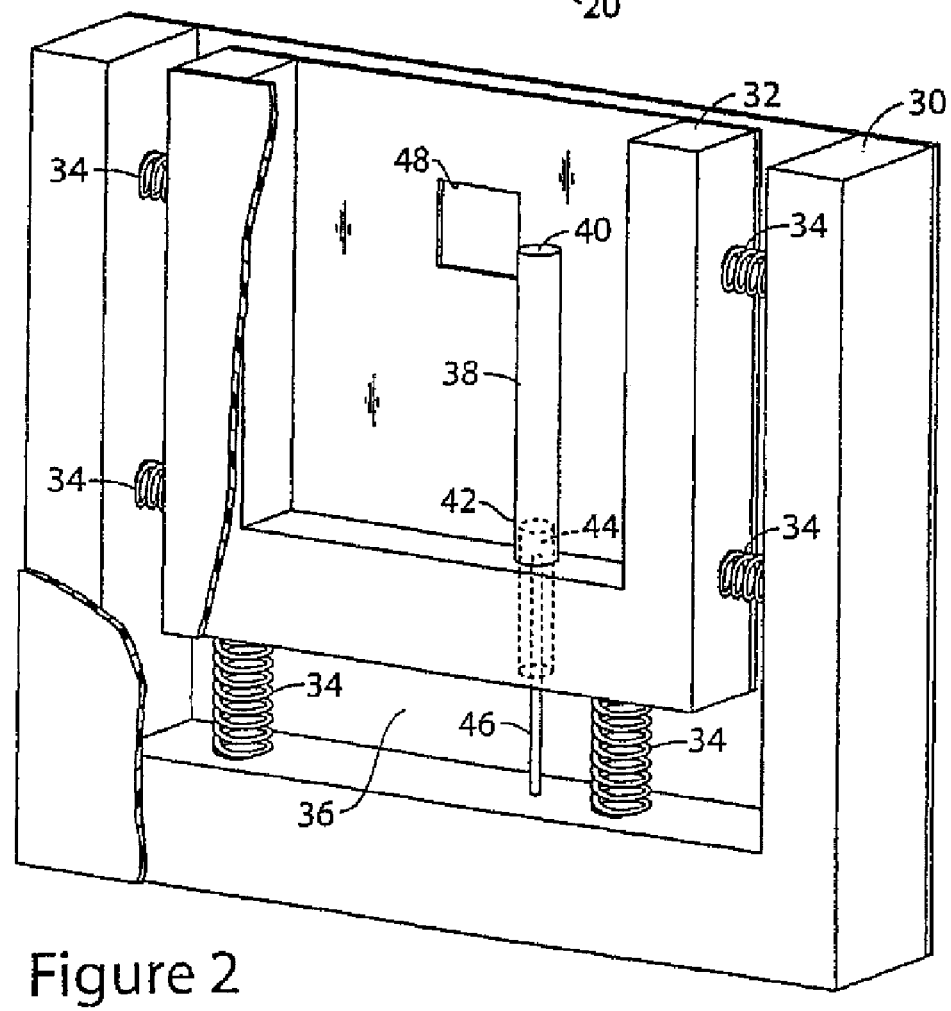
FIG. 2 is a drawing of the chamber in the sampling device where the cartridge is loaded.

FIG. 2 shows the chamber (30) in the sampling device where the cartridge is loaded. The cartridge is loaded on a socket (32) suspended with springs (34) and sits in slot (36). The launcher (38) is attached to the socket (32). The launcher has a proximal end (40) and a distal end (42). The launcher is any mechanical (such as spring or cam driven) or electrical (such as electromagnetically or electronically driven) means for advancing, stopping, and retracting the lancet. There is a clearance (44) between the distal end of the launcher (42) and the sensor (46) which is attached to the chamber (30). The socket (32) also contains the system for analyzing the blood (48) which corresponds to the active area (28) on the cartridge (10) when it is loaded into the socket (32).

Figure 3:
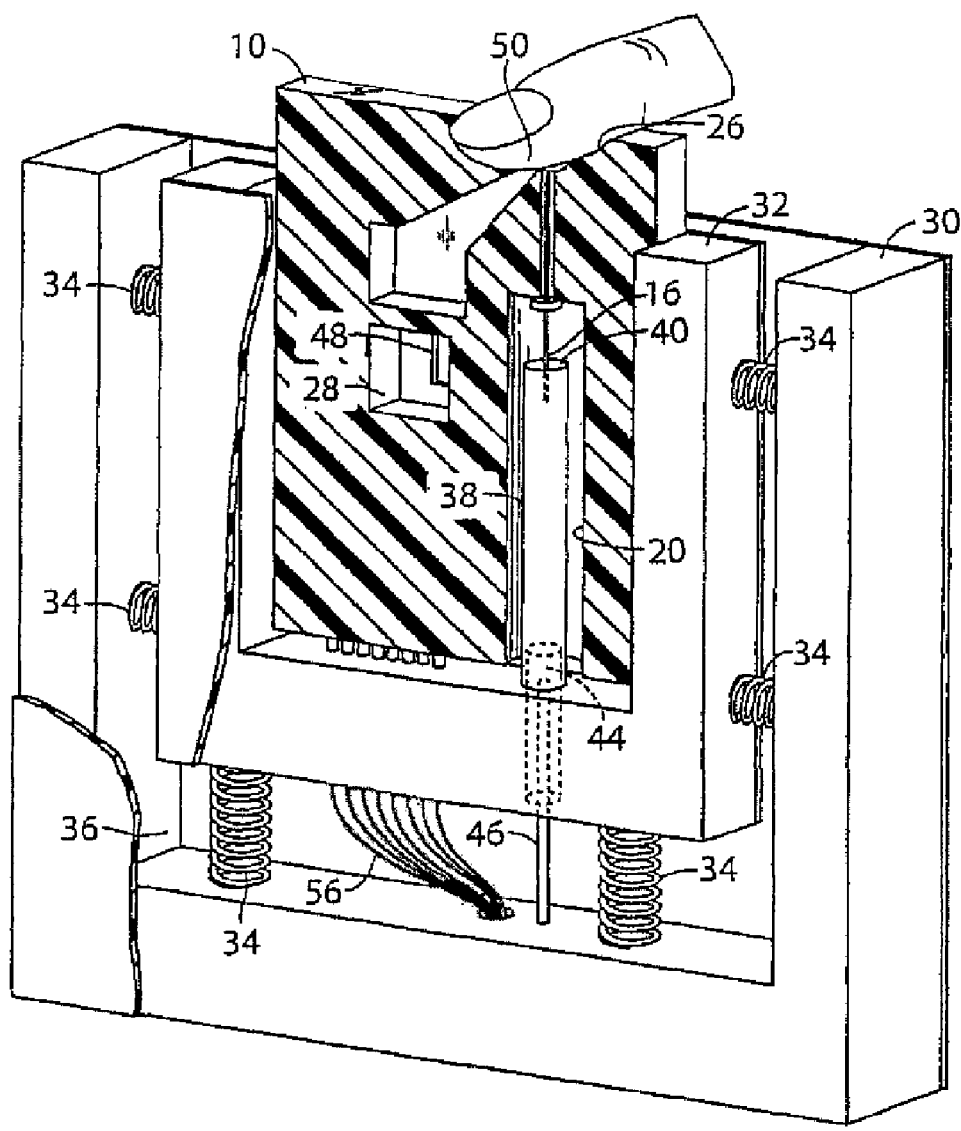
FIG. 3 is a drawing of the cartridge loaded into the sampling device.

FIG. 3 shows a cartridge (10) loaded into the socket (32). The active area (28) and system for analyzing the blood (48) overlap. The launcher (38) fits into the cavity (20). The proximal end (40) of the launcher (38) abuts the distal end (16) of the lancet (12). The patient's finger (50) sits on the ergonomically contoured surface (26).

Figure 4:
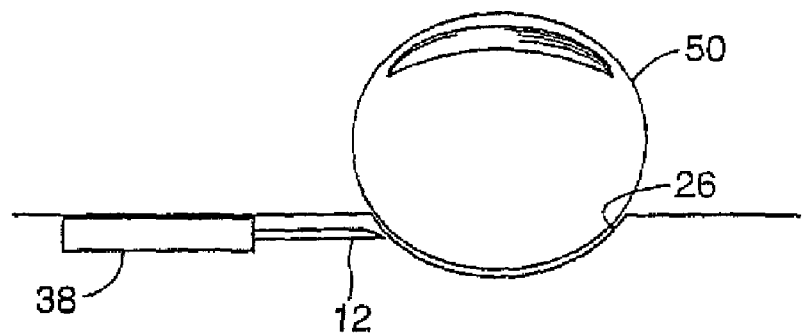
FIG. 4 is a drawing of an alternate lancet configuration.

FIG. 4 shows a drawing of an alternate lancet configuration where the lancet (12) and launcher (38) are oriented to lance the side of the finger (50) as it sits on the ergonomically contoured surface (26).

Figure 5:
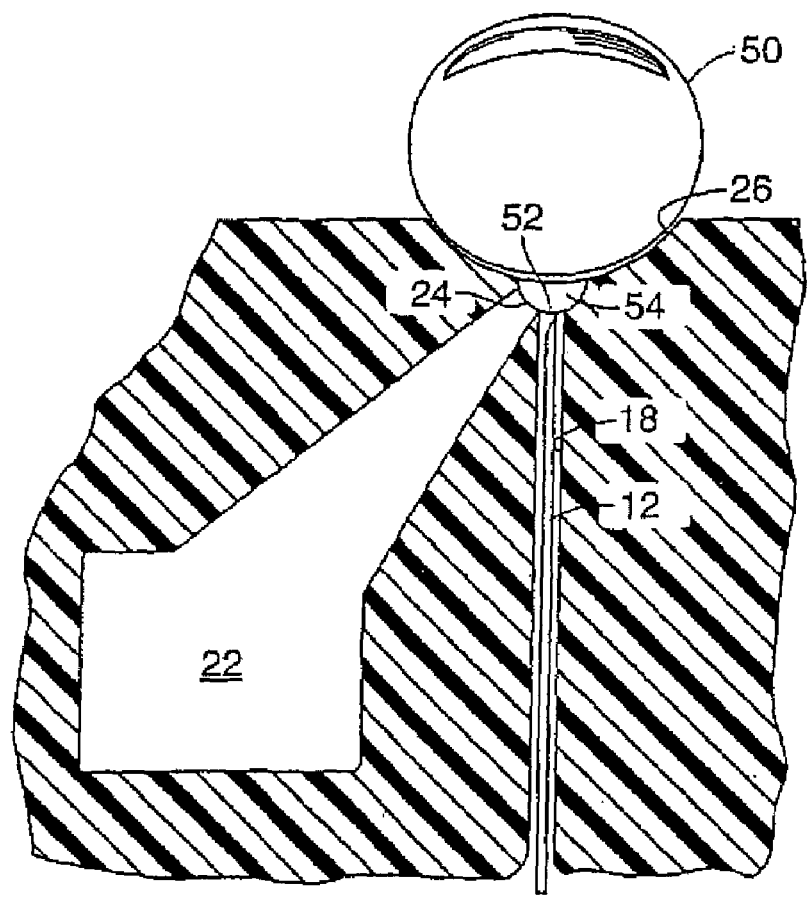
FIG. 5 is a drawing of the orifice and ergonomically contoured sampling area.

FIG. 5 illustrates with exploded detail the orifice (52) and ergonomically contoured surface (26). The conduit (18) has an orifice (52) which opens on a blood well (54). The narrow opening (24) of the reservoir (22) also opens on the blood well (54). The diameter of the narrow opening (24) is significantly greater than the diameter of the orifice (52) which is substantially the same diameter as the diameter of the lancet (12). After the lancet is retracted, the blood flowing from the finger (50) will collect in the blood well (54). The lancet (12) will have been retracted into the orifice (52) effectively blocking the passage of blood down the orifice (52). The blood will flow from the blood well (54) through the narrow opening (24) into the reservoir (22).

Figure 6:
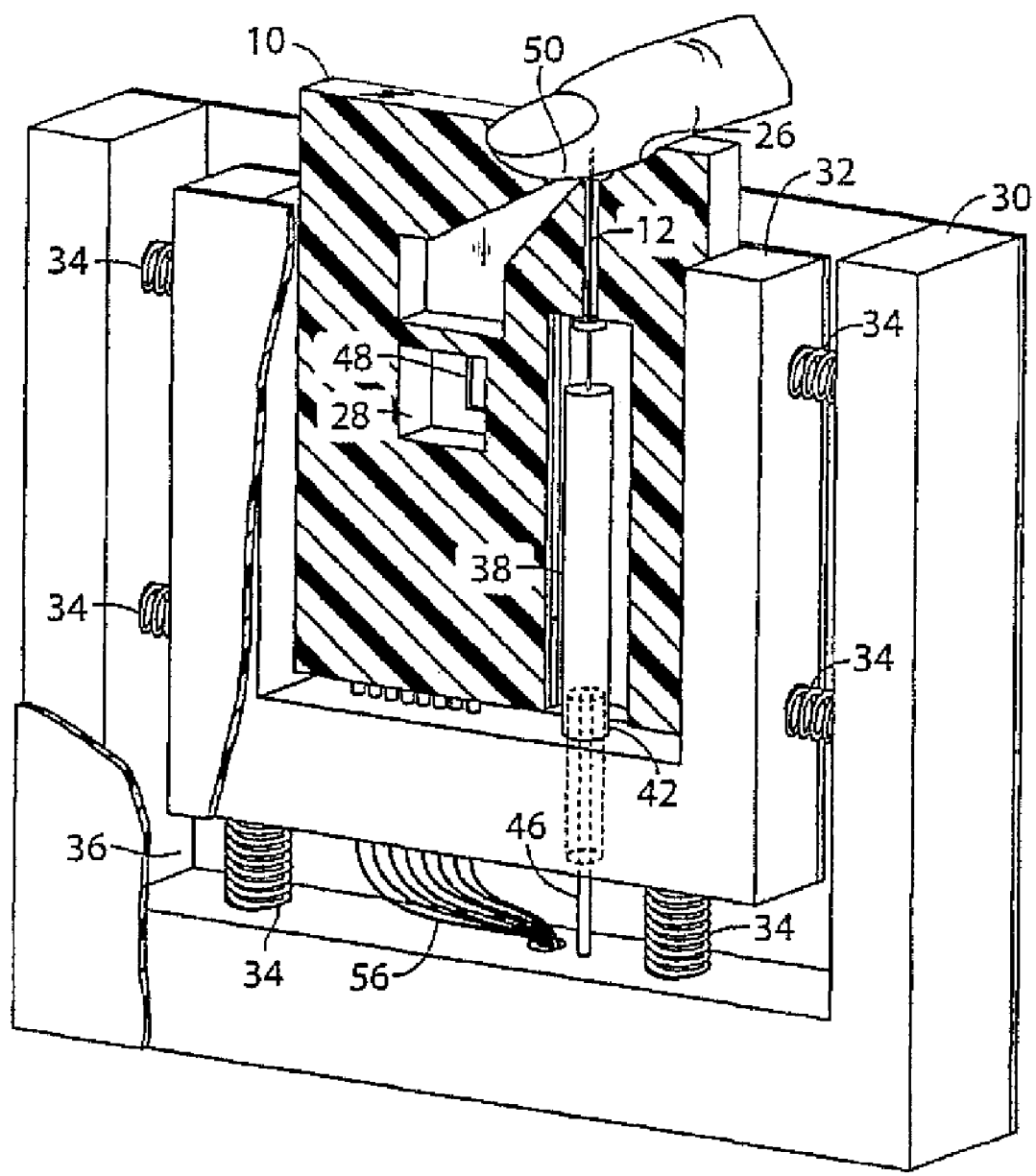
FIG. 6 is a drawing of the lancing event.

FIG. 6 shows a drawing of the lancing event. The patient applies pressure by pushing down with the finger (50) on the ergonomically contoured surface (26). This applies downward pressure on the cartridge (10) which is loaded into the socket (32).

As the socket (32) is pushed downward it compresses the springs (34). The sensor (46) makes contact with the distal end (42) of the launcher (38) and thereby detects the presence of the finger on the ergonomically contoured surface. Detection means sensing using electrical means. The sensor is a piezoelectric device which detects this pressure and sends a signal to circuit (56) which actuates the launcher (38) and advances and then retracts the lancet (12) lancing the finger (50). In another embodiment, the sensor (46) is an electric contact which closes a circuit when it contacts the launcher (38) activating the launcher (38) to advance and retract the lancet (12) lancing the finger (50).

Activating means beginning the lancing event, which consists of advancing, stopping, and retracting the lancet.

An embodiment of the invention is a method of sampling which reduces the number of steps that must be taken by a patient to obtain a sample and analysis of the sample. First, the patient loads a cartridge with an embedded sterile lancet into the device. Second, the patient initiates a lancing cycle by turning on the power to the device or by placing the finger to be lanced on the ergonomically contoured surface and pressing down. Initiation means arming the device. This initiation prompts the sensor.

Prompting means that the sensor is made operational and given control to activate the launcher. Prompting is a safety precaution to avoid unintentionally launching the lancet.

The sensor is unprompted when the lancet is retracted after its lancing cycle to avoid multiple lancing events that would cause unnecessary pain and obstruct the collection of the blood sample. The lancing cycle consists of arming, advancing, stopping and retracting the lancet, and collecting the blood sample in the reservoir. The cycle is complete once the blood sample has been collected in the reservoir. Third, the patient presses down on the cartridge which forces the launcher to make contact with the sensor and activates the launcher. The lancet then pierces the skin and the reservoir collects the blood sample. The patient is then optionally informed to remove the finger by an audible signal such as a buzzer or a beeper, and/or a visual signal such as an LED or a display screen. The patient can then dispose of all the contaminated parts by removing the cartridge and disposing of it. In another embodiment, multiple cartridges may be loaded into the sampling device in the form of a cassette. The patient is informed by the device as to when to dispose of the entire cassette after the analysis is complete.

Other embodiments of the invention will be apparent to those skilled in the art from consideration of the specification and practice of the invention disclosed herein.

It is intended that the specification and examples be considered as exemplary only, with a true scope and spirit of the invention being indicated by the following claims.

The invention claimed is:
1. A sampling device comprising:
a disposable cartridge comprising a conduit, a reservoir for collecting a blood sample, said reservoir having a narrow opening on an ergonomically contoured surface of said cartridge;
a lancet for obtaining a blood sample from a finger, said lancet having a first distal end and a first proximal end, said lancet embedded within said conduit, said conduit running from a cavity within said cartridge to an orifice on said ergonomically contoured surface, said first proximal end used to pierce said finger, said lancet oriented so that the first distal end is longitudinal to the cavity, and the first proximal end is longitudinal to the orifice;
a launcher on said device fitted within said cavity, said launcher having a second proximal end and a second distal end; said second proximal end connecting to said first distal end; and
a sensor affixed to said device, said sensor adjacent to the second distal end of the launcher, said sensor detecting said finger on the ergonomically contoured surface; said sensor initiating a lancing cycle.
2. A sampling device according to claim 1 wherein said device further comprises:

a system for analyzing the blood sample, by channeling blood from said reservoir to an active area within said cartridge, said active area overlapping said system.

3. A sampling device according to claim 1 wherein:
said sensor comprising a piezoelectric circuit, said circuit contacting the second distal end when the finger applies pressure on said ergonomically contoured surface.

4. A sampling device according to claim 1 wherein:
said sensor comprising an electric circuit, said circuit contacting the second distal end when the finger applies pressure on said ergonomically contoured surface.

* * * * *